United States Patent [19]

Sohda et al.

[11] Patent Number: 5,550,138
[45] Date of Patent: Aug. 27, 1996

[54] CONDENSED THIADIAZOLE DERIVATIVE, METHOD OF ITS PRODUCTION, AND USE THEREOF

[75] Inventors: Takashi Sohda; Zen-ichi Terashita, both of Osaka; Yu Momose; Yukio Fujisawa, both of Hyogo; Junji Mizoguchi, Osaka, all of Japan

[73] Assignee: Takeda Chemical Industries, Ltd., Osaka, Japan

[21] Appl. No.: 39,579

[22] Filed: Mar. 23, 1993

[30] Foreign Application Priority Data

Mar. 25, 1992 [JP] Japan ..................... 4-067615
Feb. 19, 1993 [JP] Japan ..................... 5-030872

[51] Int. Cl.⁶ ................... C07D 513/04; A61K 31/435
[52] U.S. Cl. .......................... 514/361; 548/130
[58] Field of Search .................. 548/130; 514/361

[56] References Cited

FOREIGN PATENT DOCUMENTS 239064  9/1987  European Pat. Off. .
60-246389  12/1985  Japan .
62-263185  11/1987  Japan .

OTHER PUBLICATIONS

*Biochemical Pharmacology*, vol. 44, No. 6, Sep. 25, 1992, pp. 1201–1207.
*Chemical Abstracts*, vol. 114, No. 3, Jan. 21, 1991, p. 696, Abstract No. 23848u.

*Primary Examiner*—Sharon Gibson
*Assistant Examiner*—Catherine Kilby Scalzo
*Attorney, Agent, or Firm*—Foley & Lardner

[57] ABSTRACT (1) a compound represented by the following formula (I):

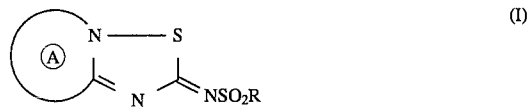

wherein R represents a hydrocarbon group or heterocyclic group which may be substituted; the ring A represents a pyridine ring having a substituent or a thiazole ring which may be substituted; or a pharmaceutically acceptable salt thereof, and a method of its production, and (2) an endothelin receptor antagonist, an cathepsin B inhibitor or a bone resorption suppressor having as an active ingredient a compound represented by the following formula (I'):

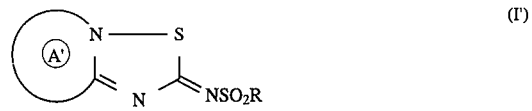

wherein R has the same definition as in term (1); the ring A' represents a pyridine ring or thiazole ring which may be substituted; or a pharmaceutically acceptable salt thereof.

16 Claims, No Drawings

CONDENSED THIADIAZOLE DERIVATIVE, METHOD OF ITS PRODUCTION, AND USE THEREOF

FIELD OF THE INVENTION

The present invention relates to new compounds useful as exhibiting endothelin receptor antagonistic action, cathepsin B inhibiting action and bone resorption inhibitory action, a method of their production and use thereof.

BACKGROUND OF THE INVENTION

Although various peptides have been reported as exhibiting endothelin receptor antagonistic action, there have been reported no non-peptide compounds but anthraquinone derivatives (the official gazette of EP Publication No. 405421 A).

Osteoporosis is a pathologic state or disease involving any symptom or risk due to quantitative reduction in bone exceeding a certain degree. Major symptoms are spinal kyphosis, and fractures of dorsolumbar bone and vertebral centra, femoral neck, lower end of radius, ribs, upper end of humerus, and other bones. In bone tissue, bone destruction occurs constantly with a good balance between bone formation and resorption; osteoblasts and osteoclasts play key roles in bone formation and bone resorption, respectively. If bone resorption surpasses bone formation as a result of the deterioration of the bone destruction balance, a quantitative reduction in bone occurs. Also, inflammatory joint diseases such as chronic rheumatoid arthritis involve accentuated bone resorption, posing a major clinical problem. Drugs suppressing bone resorption are therefore expected to serve well in the prevention and treatment of osteoporosis and inflammatory joint diseases such as chronic rheumatoid arthritis. Traditionally, bone resorption inhibitory agents such as estrogens and calcitonin have been used to treat osteoporosis. To treat inflammatory joint diseases chemotherapeutically, there have been used steroids such as cortisone and other adrenocortical hormones, non-steroidal anti-inflammatory agents such as aspirin, piroxicam and indomethacin, aurothiomalate and other gold agents, antirheumatic agents such as chloroquine preparations and D-penicillamine, anti-gout agents such as colchicine, and immunosuppressants such as cyclophosphamide, azathioprine, methotrexate and levamisole. However, these therapeutic agents fail to have a satisfactory effect in some cases, due to limitation on the subject or to uncertain efficacy. There is therefore a need of a new preventive/therapeutic method for accentuated bone resorption.

It has recently been suggested that cathepsin B, a lysosome cysteine protease, is involved in joint destruction due to inflammatory joint disease [Biochemical Pharmacology, 44, 1201 (1992)]. Also, cathepsin B is thought of as causing intractable muscle collapsing diseases such as myodystrophy and vacuolar distal myopathy. It is also among the enzymes involved in the formation of senile plaques in the brain of patients with Alzheimer's disease. Cathepsin B inhibitors are therefore expected to be useful against these diseases. Traditionally, leupeptin, antipain etc., and epoxysuccinic acid derivatives such as those disclosed in Japanese Patent Unexamined Publication Nos. 304074/1990, 304075/1990 and 304085/1990 are known to exhibit cathepsin B inhibitory action.

On the other hand, among condensed thiadiazole derivatives having a sulfonylimino group are 2-sulfonylimino-2H-[1,2,4]thiadiazolo[2, 3-a]pyrimidine and triazine derivatives, which are known to serve as herbicides (see Japanese Patent Unexamined Publication Nos. 263185/1987 and 10795/1988). Also, Japanese Patent Unexamined Publication No. 246389/1985 describes a 2-sulfonylimino-2H-[1,2,4]thiadiazolo[2, 3-a]pyrimidine derivative, a compound exhibiting platelet aggregation inhibitory and cardiotonic actions, represented by the following formula:

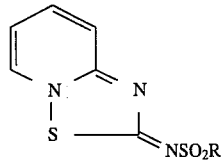

wherein R represents a lower alkyl group or a phenyl group which may be substituted by a lower alkyl group or halogen. However, none of these reports discloses endothelin receptor antagonistic action, cathepsin B inhibiting action and bone resorption inhibitory action.

OBJECT OF THE INVENTION

The present invention aims at providing new thiadiazole derivatives useful as exhibiting endothelin receptor antagonistic action, cathepsin B inhibiting action and bone resorption inhibitory action, a method of their production and use thereof.

Through intensive investigations from the above viewpoint, the present inventors found that a new condensed thiazole derivative exhibits excellent endothelin receptor antagonistic action, potent cathepsin B inhibiting action and potent bone resorption inhibitory action, and developed the present invention.

SUMMARY OF THE INVENTION

Accordingly, the present invention provides:

(1) a compound represented by the following formula (I):

wherein R represents a hydrocarbon group or heterocyclic group which may be substituted; the ring A represents a pyridine ring having a substituent or a thiazole ring which may be substituted; or a pharmaceutically acceptable salt thereof.

(2) a method of producing a compound represented by the following formula (I):

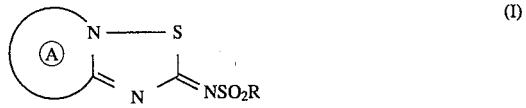

wherein R and the ring A have the same definitions as in above (1), or a pharmaceutically acceptable salt thereof, by cyclizing a compound represented by the following formula (II):

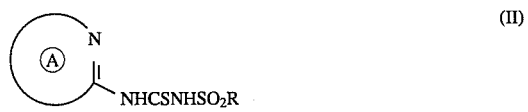

wherein R and the ring A have the same definitions as in above (1), (3) an endothelin receptor antagonist comprising as an active ingredient a compound represented by the following formula (I'):

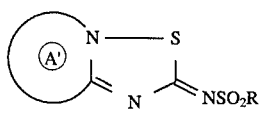

wherein R has the same definition as in above (1); the ring A' represents a pyridine ring or thiazole ring which may be substituted, or a pharmaceutically acceptable salt thereof, (4) a cathepsin B inhibitor comprising as an active ingredient a compound represented by the following formula (I'):

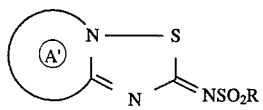

wherein R has the same definition as in above (1); the ring A' represents a pyridine ring or thiazole ring which may be substituted, or a pharmaceutically acceptable salt thereof, and (5) a bone resorption suppressor comprising as an active ingredient a compound represented by the following formula (I'):

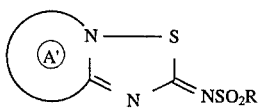

wherein R has the same definition as in above (1); the ring A' represents a pyridine ring or thiazole ring which may be substituted; or a pharmaceutically acceptable salt thereof.

DESCRIPTION OF THE PREFERRED EMBODIMENT

Such pharmaceutically acceptable salts include salts with an inorganic base, salts with organic base, salts with an inorganic acid, salts with an organic acid and salts with a basic or acidic amino acid. Preferable salts with an inorganic base include alkali metal salts such as the sodium salt, alkaline earth metal salts such as the calcium salt and the magnesium salt, aluminum salt, and ammonium salt. Preferable salts with an organic base include salts with trimethylamine, triethylamine, pyridine, picoline, ethanolamine, diethanolamine, triethanolamine, dicyclohexylamine and N, N'-dibenzylethylenediamine. Preferable salts with an inorganic acid include the hydrochloride, hydrobromate, nitrate, sulfate and phosphate salts. Preferable salts with an organic acid include the formate, acetate, trifluoroacetate, fumarate, oxalate, tartrate, maleate, citrate, succinate, malate, methanesulfonate, benzenesulfonate and p-toluenesulfonate salts. Preferable salts with a basic amino acid include salts with arginine, lysine and ornithine. Preferable salts with an acidic amino acid include aspartate and glutamate.

Terms used in the present specification are described below.

The term "lower" means 1 to 6 carbon atoms, unless otherwise stated, and a "hydrocarbon group" is an aliphatic chain hydrocarbon group, alicyclic hydrocarbon group, aryl group or the like.

Aliphatic chain hydrocarbon groups include linear or branched aliphatic hydrocarbon groups, such as alkyl groups, alkenyl group and alkinyl groups, with preference given to lower alkyl groups, lower alkenyl groups, lower alkinyl groups and others.

Preferable lower alkyl groups include $C_{1-6}$ alkyls such as methyl, ethyl, propyl, isopropyl, butyl, isobutyl, sec-butyl, tert-butyl, pentyl, isopentyl, neopentyl, tert-pentyl, 1-ethylpropyl, hexyl, isohexyl, 1,1-dimethylbutyl, 2,2-dimethylbutyl, 3,3-dimethylbutyl and 2-ethylbutyl, with preference given to methyl, ethyl, propyl, isopropyl, butyl, isobutyl and others.

Preferable lower alkenyl groups include $C_{2-6}$ alkenyls such as vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl, with preference given to vinyl, allyl, isopropenyl, 2-methyl- 1-propenyl and others.

Preferable lower alkinyl groups include $C_{2-6}$ alkinyls such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl, with preference given to ethynyl, 1-propynyl, 2-propynyl and others.

Alicyclic hydrocarbon groups are saturated or unsaturated alicyclic hydrocarbon groups such as cycloalkyl groups, cycloalkenyl groups and cycloalkadienyl groups.

Preferable cycloalkyl groups include $C_{3-6}$ cycloalkyls such as cyclopropyl, cyclobutyl, cyclopentyl and cyclohexyl, and cycloheptyl, cyclooctyl, bicyclo[2, 2, 1]heptyl, bicyclo[2,2,2]octyl, bicyclo[3,2,1]octyl, bicyclo[3,2,2]nonyl, bicyclo[3,3,1]nonyl, bicyclo[4,2,1]nonyl and bicyclo[4,3,1]decyl.

Preferable cycloalkenyl groups include 2-cyclopenten-1-yl, 3-cyclopenten- 1-yl, 2-cyclohexen-1-yl and 3-cyclohexen-1-yl.

Preferable cycloalkadienyl groups include 2,4-cyclopentadien-1-yl, 2, 4-cyclohexadien-1-yl and 2,5-cyclohexadien-1-yl Aryl groups are monocyclic or condensed polycyclic aromatic hydrocarbon groups. Preferable aryl groups include phenyl, naphthyl, anthryl, phenanthryl and acenaphthylenyl, with preference given to phenyl, 1-naphthyl, 2-naphthyl and others.

The heterocyclic group is an aromatic heterocyclic group having at least one hetero atom of oxygen, sulfur or nitrogen as a ring-forming atom (ring atom), or a saturated or unsaturated non-aromatic heterocyclic group (aliphatic heterocyclic group).

Aromatic heterocyclic groups are aromatic monocyclic heterocyclic groups and aromatic condensed heterocyclic groups.

Preferable aromatic monocyclic heterocyclic groups include furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl and triazinyl.

Preferable aromatic condensed heterocyclic groups include benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolyl, quinazolyl, quinoxalinyl, phthalazinyl, naphthilizinyl, purinyl, butelinidyl, carbazolyl, α-carbolinyl, β-carbolinyl, γ-carbolinyl, acridinyl, phenoxazinyl, phenothiazinyl, phenazinyl, phenoxthinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl and 1,2,4-triazolo[4,3-b]pyridazinyl.

Preferable non-aromatic heterocyclic groups include oxalanyl, azetidinyl, oxacetanyl, thioethanyl, pyrrolidinyl, tetrahydrofuryl, thiolanyl, piperidyl, tetrahydropyranyl, morpholinyl, thiomorpholinyl and piperazinyl.

Acyl groups are aliphatic acyl groups such as alkanoyl groups, alkenoyl groups, cycloalkanecarbonyl groups and alkanesulfonyl groups, aromatic acyl groups such as aroyl groups, arylalkanoyl groups, arylalkenoyl groups and allenesulfonyl groups, aromatic heterocyclic carbonyl groups, and aromatic heterocyclic alkanoyl groups.

Alkanoyl groups are alkylcarbonyl groups. Preferable alkanoyl groups include lower alkanoyl groups such as formyl, acetyl, propionyl, butyryl, isobutyryl, valeryl, isovaleryl, pivaloyl and hexanoyl.

Alkenoyl groups are alkenylcarbonyl groups. Preferable alkenoyl groups include lower alkenoyl groups such as acryloyl, methacryloyl, crotonoyl and isocrotonoyl.

Cycloalkanecarbonyl groups are cycloalkylcarbonyl groups. Preferable cycloalkanecarbonyl groups include cyclopropanecarbonyl groups, cyclobutanecarbonyl groups, cyclopentanecarbonyl groups and cyclohexanecarbonyl groups.

Alkanesulfonyl groups are alkylsulfonyl groups. Preferable alkanesulfonyl groups include lower alkanesulfonyl groups such as mesyl, ethanesulfonyl and propanesulfonyl.

Aroyl groups are arylcarbonyl groups. Preferable aroyl groups include benzoyl, p-toluoyl, 1-naphthoyl and 2-naphthoyl.

Arylalkanoyl groups are alkylcarbonyl groups substituted by an aryl group. Preferable arylalkanoyl groups include aryl lower alkanoyl groups such as phenylacetyl, phenylpropionyl, hydroatropoyl and phenylbutyryl.

Arylalkenoyl groups are alkenylcarbonyl groups substituted by an aryl group. Preferable arylalkenoyl groups include aryl lower alkenoyl groups such as cinnamoyl and atropoyl.

Arenesulfonyl groups are arylsulfonyl groups. Preferable arenesulfonyl groups include benzenesulfonyl groups and p-toluenesulfonyl groups.

Preferable aromatic heterocyclic carbonyl groups include furoyl, thenoyl, nicotinoyl, isonicotinoyl, pyrrolecarbonyl, oxazolecarbonyl, imidazolecarbonyl and pyrazolecarbonyl.

Aromatic heterocyclic alkanoyl groups are alkylcarbonyl groups substituted by an aromatic heterocyclic group. Preferable aromatic heterocyclic alkanoyl groups include aromatic heterocyclic lower alkanoyl groups such as thienylacetyl, thienylpropanoyl, furylacetyl, thiazolylacetyl, 1,2,4-thiadiazolylacetyl and pyridylacetyl.

The carboxyl group which may be esterified is a lower alkoxycarbonyl group or an aryloxycarbonyl group. Preferable carboxyl groups which may be esterified include methoxycarbonyl, ethoxycarbonyl, propoxycarbonyl, phenoxycarbonyl and 1-naphthoxycarbonyl.

Example substituents in the amino group which may be substituted include lower alkyl groups, cycloalkyl groups, aryl groups, aromatic heterocyclic groups, aralkyl groups, acyl groups, and carboxyl groups which may be esterified. Also, the two substituents on a nitrogen atom may cooperate therewith to form a cyclic amino group. Examples of such cyclic amino groups include 1-azetidinyl, 1-pyrrolidinyl, piperidino, morpholino, 1-piperazinyl, and 1-piperazinyl having a lower alkyl group, an aralkyl group, an aryl group or the like at the 4-position.

Substituents in the carbamoyl group which may be substituted include the same substituents as those specified for the amino group which may be substituted.

Substituents for the hydroxyl group which may be substituted, and for the thiol group which may be substituted, include the same substituents as those specified for the amino group which may be substituted.

Preferable halogens include fluorine, chlorine, bromine and iodine, with preference given to fluorine, chlorine, bromine and others.

The aralkyl group is an alkyl group having a substituent aryl group (arylalkyl group). Said aryl group may have one or two substituents at any possible positions. Such additional substituents include lower alkyl groups, lower alkenyl groups, lower alkinyl groups, cycloalkyl groups, aryl groups, aromatic heterocyclic groups, aralkyl groups, amino groups which may be substituted, acyl groups, carbamoyl groups which may be substituted, hydroxyl groups which may be substituted, carboxyl groups which may be esterified, thiol groups which may be substituted, sulfo groups, cyano groups, nitro groups and halogens, with preference given to halogens and lower alkyl groups, more preferably $C_{1-3}$ alkyls such as methyl, ethyl and propyl. Preferable aralkyl groups include benzyl, phenethyl, 3-phenylpropyl, (1-naphthyl) methyl and (2-naphthyl) methyl, with preference given to benzyl, phenethyl and others.

With respect to the above formula, the hydrocarbon group represented by R, which may be substituted, is exemplified by aliphatic hydrocarbon groups, alicyclic hydrocarbon groups and aryl groups, with preference given to aliphatic hydrocarbon groups and aryl groups. It is preferred that the aliphatic hydrocarbon group contains carbon atoms of less than 10, preferably less than 8.

Example heterocyclic groups represented by R, which may be substituted, include aromatic heterocyclic groups and non-aromatic heterocyclic groups (aliphatic heterocyclic groups), with preference given to aromatic heterocyclic groups. Of the aromatic heterocyclic groups thienyl, pyridyl, pyrimidinyl and furyl are preferred.

This hydrocarbon group represented by R may have 1 or more, preferably 1 to 3 substituents at any possible positions. Examples of such substituents include cycloalkyl groups, aryl groups, aromatic heterocyclic groups, acyl groups, carboxyl groups which may be esterified, amino groups which may be substituted, carbamoyl groups which may be substituted, hydroxyl groups which may be substituted, thiol groups which may be substituted, sulfo groups, cyano groups, nitro groups and halogens. In case that said hydrocarbon group is an alicyclic hydrocarbon group or an aryl group, further examples of substituents include lower alkyl groups, lower alkenyl groups, lower alkinyl groups and aralkyl groups.

This heterocyclic group represented by R may have 1 or more, preferably 1 to 3 substituents at any possible positions. Examples of such substituents include lower alkyl groups, lower alkenyl groups, lower alkinyl groups, cycloalkyl groups, aryl groups, aromatic heterocyclic groups, aralkyl groups, acyl groups, carboxyl groups which may be esterified, amino groups which may be substituted, carbamoyl groups which may be substituted, hydroxyl groups which may be substituted, thiol groups which may be substituted, sulfo groups, cyano groups, nitro groups and halogens.

Compounds having a pyridine ring represented by the ring A in the above formula, which ring has a substituent, include those having a ring represented by the following formula:

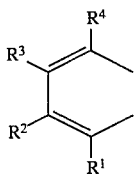

wherein $R^1$, $R^2$, $R^3$ and $R^4$ independently represent hydrogen, halogen, a hydroxyl group which may be substituted, an amino group which may be substituted, a thiol which may be substituted, a carboxyl group which may be esterified, a hydrocarbon group which may be substituted, or a heterocyclic group which may be substituted; adjoining substituents may cooperate to form a ring. Examples of such hydrocarbon groups, which may be substituted, include aliphatic hydrocarbon groups, alicyclic hydrocarbon groups and aryl groups, with preference given to aliphatic hydrocarbon groups and aryl groups. Examples of such heterocyclic groups, which may be substituted, include aromatic heterocyclic groups and non-aromatic heterocyclic groups (aliphatic heterocyclic groups), with preference given to aromatic heterocyclic groups. Of the aromatic heterocyclic groups theinyl, pyridyl, pyrimidinyl and furyl are preferred. The number and kind of substituents are the same as those specified for R. Rings formed by adjoining substituents in cooperation include the following:

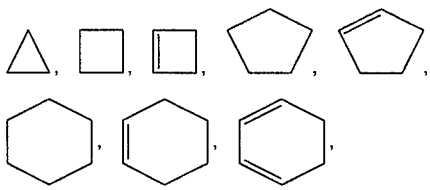

with preference given to the following:

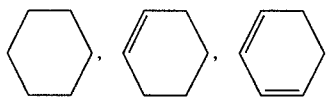

Said ring may have one or more substituents, preferably 1 or 2 substituents at any possible positions. Such substituents include methyl, ethyl and propyl.

Compounds having a thiazole ring represented by the ring A in the above formula, which ring may be substituted, include those having a ring represented by the following formula:

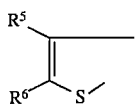

wherein $R^5$ and $R^6$ independently represent hydrogen, halogen, a carboxyl group which may be esterified, a hydrocarbon group which may be substituted, or a heterocyclic group which may be substituted; adjoining substituents may cooperate to form a ring. Examples of such hydrocarbon groups, which may be substituted, include aliphatic hydrocarbon groups, alicyclic hydrocarbon groups and aryl groups, with preference given to aliphatic hydrocarbon groups and aryl groups. Examples of such heterocyclic groups, which may be substituted, include aromatic heterocyclic groups and non-aromatic heterocyclic groups (aliphatic heterocyclic groups), with preference given to aromatic heterocyclic groups. Of the aromatic heterocyclic groups thienyl, pyridyl, pyrimidinyl, furyl, indolyl and isoindolyl are preferred.

The aryl group in said hydrocarbon group may be a partially reduced one, such as tetrahydro-2-naphthyl.

Said hydrocarbon group may have 1 or more, preferably 1 to 3 substituents at any possible positions. Examples of such substituents include cycloalkyl groups, aryl groups, aromatic heterocyclic groups, acyl groups, carboxyl groups which may be esterified, amino groups which may be substituted, carbamoyl groups which may be substituted, hydroxyl groups which may be substituted, thiol groups which may be substituted, sulfo groups, cyano groups, nitro groups and halogens. In case that said hydrocarbon group is an alicyclic hydrocarbon group or an aryl group, further examples of substituents include lower alkyl groups, lower alkenyl groups, lower alkinyl groups and aralkyl groups. Further, in case that said hydrocarbon group is an aryl group, two adjoining hydroxyl groups, which may be substituted, on the aryl group may cooperate therewith to form a heterocyclic ring. An example of such rings is the following formula:

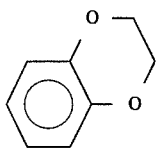

Said heterocyclic group may have 1 or more, preferably 1 to 3 substituents at any possible positions. Examples of such substituents include lower alkyl groups, lower alkenyl groups, lower alkinyl groups, cycloalkyl groups, aryl groups, aromatic heterocyclic groups, aralkyl groups, acyl groups, carboxyl groups which may be esterified, amino groups which may be substituted, carbamoyl groups which may be substituted, hydroxyl groups which may be substituted, thiol groups which may be substituted, sulfo groups, cyano groups, nitro groups and halogens.

Of the substituents in the hydrocarbon group which may be substituted, each of lower alkyl groups and aryl groups may have additional one or two of halogens, carboxyl groups which may be esterified and carbamoyl groups which may be substituted at any possible positions. Examples of such carboxyl groups which may be esterified include methoxycarbonyl, ethoxycarbonyl and propoxycarbonyl. Substituents for the carbamoyl group which may be substituted include $C_{1-3}$ alkyls which may be substituted by an alkoxycarbonyl (e.g., ethoxycarbonyl, methoxycarbonyl, propoxycarbonyl), and phenyls which may be substituted by a $C_{1-3}$ alkyl or halogen.

The acyl group in the substituent for the hydrocarbon group which may be substituted may be an allenesulfinyl resulting from reduction of allenesulfonyl, such as a benzenesulfinyl group or a p-toluenesulfinyl group.

The carboxyl group which may be esterified in the substituent for the hydrocarbon group which may be substituted may be an aryl lower alkoxycarbonyl, such as benzyloxycarbonyl, phenylethoxycarbonyl or phenylpropoxycarbonyl.

The substituent in the carbamoyl group which may be substituted in the substituent for the hydrocarbon group which may be substituted may be a tetrahydronaphthyl having one or two $C_{1-3}$ alkyls at any possible positions. Of the substituents in the carbamoyl group which may be substituted, lower alkyls, cycloalkyl groups and aryl groups may have at any possible positions one or two of carboxyl groups which may be esterified, cycloalkyl groups and hydroxyl groups whch may be substituted. In case that the substituent in the carbamoyl group which may be substituted is a cycloalkyl group or an aryl group, said substituent may have $C_{1-3}$ alkyl groups which may be substituted. The substituent for the $C_{1-3}$ alkyl group which may be substituted is exemplified by a phosphono group which may be esterified and a carboxyl group which may be esterified. Examples of such phosphono groups, which may be esterified, include ethylphosphono, diethylphosphono, methylphosphono or dimethylphosphono group. Two of the substituents in the carbamoyl group which may be substituted may cooperate with the adjacent nitrogen atom to form a heterocyclic ring which may contain another hetero atom (e.g., oxygen, nitrogen, sulfur). Such heterocyclic rings include the following:

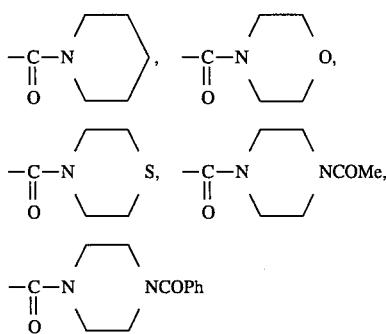

with preference given to the following:

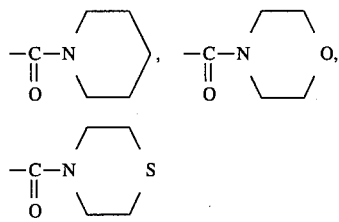

Said heterocyclic ring may have 1 to 2 substituents at any posssible positions. Examples of such substituents include lower alkyl groups, carboxyl groups which may be esterified, hydroxyl groups which may be substituted and carbamoyl groups which may be substituted.

Of the substituents in the hydrocarbon group which may be substituted, the substituent in the hydroxyl group which may be substituted may be a halogen. Of the substituents in the hydroxyl group which may be substituted, lower alkyls may have 1 to 2 aryl groups which may be substituted at any possible positions. Examples of the substituents in the aryl group which may be substituted include halogens and $C_{1-3}$ alkyls.

Rings formed by the adjoining substituents include the following:

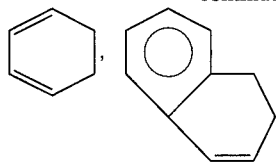

with preference given to the following:

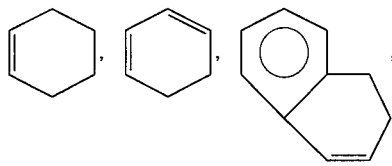

Said ring may have one or two substituents at any possible positions. Such substituents include methyl, ethyl and propyl.

The pyridine ring represented by the ring A' in the above formula, which may have a substituent, is exemplified by a compound represented by the following formula:

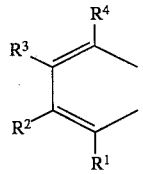

wherein $R^1$, $R^2$, $R^3$ and $R^4$ independently represent hydrogen, halogen, a hydroxyl group which may be substituted, an amino group which may be substituted, a thiol which may be substituted, a carboxyl group which may be esterified, a hydrocarbon group which may be substituted, or a heterocyclic group which may be substituted; adjoining substituents may cooperate to form a ring. Examples of said hydrocarbon group or heterocyclic group which may be substituted include the same hydrocarbon groups or heterocyclic groups specified for R. The number and kind of substituents are the same as those specified for R. Rings formed by the adjoining substituents in cooperation include the following:

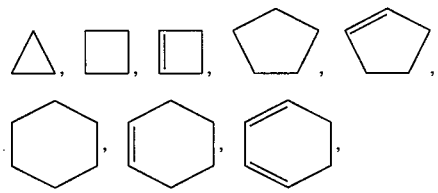

with preference given to the following:

Said ring may have one or more, preferably one or two substituents at any possible positions. Such substituents include methyl, ethyl and propyl.

The thiazole ring represented by the ring A' in the above formula, which ring may have a substituent, is exemplified by the same thiazole ring which may have a substituent as specified for the ring A'.

The present invention also provides a method of producing a compound represented by the following formula (I):

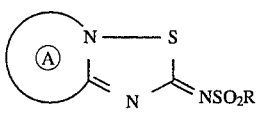

wherein R and the ring A have the same definitions as above, or a pharmaceutically acceptable salt thereof, by cyclizing a compound represented by the following formula (II):

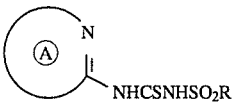

wherein R and the ring A have the same definitions as above.

Cyclization of the compound represented by formula (II) is achieved by carrying out dehydrogenation under oxidative conditions. This cyclizing reaction is carried out without being affected by the substituent in the pyridine ring or thiazole ring represented by the ring A.

This reaction is carried out by keeping compound (II) in combination with oxidant. Example oxidants include halogens such as iodine and bromine, N-halogenosuccinic imides such as N-chlorosuccinic imide and N-bromosuccinic imide, hypochlorites such as sodium hypochlorite, potassium hypochlorite and calcium hypochlorite, and sulfonyl halides such as methanesulfonyl chloride and sulfuryl chloride, with preference given to bromine and sulfuryl chloride.

Although the amount of oxidant used for this cyclizing reaction can be chosen as appropriate to complete the reaction, theoretically, it is sufficient to use it at not lower than 0.5 mol, preferably 0.5 to 3 mol per mol of the starting material compound (II).

This reaction is generally carried out in an inert solvent. Such solvents include water, alcohols such as methanol, ethanol and propanol, aromatic hydrocarbons such as benzene, toluene, xylene, nitrobenzene and chlorobenzene, hydrocarbon halides such as dichloromethane, chloroform and carbon tetrachloride, and aliphatic carboxylic acids such as formic acid and acetic acid. These solvents may be used singly or in combination at any ratio as necessary.

Reaction temperature can be chosen over the range of from about $-50°$ to $100°$ C., being preferably about $0°$ to $50°$ C. Reaction time is normally about 0.1 to 50 hours, preferably 0.2 to 5 hours, A compound represented by the following formula (I'):

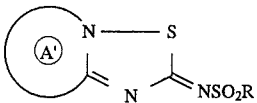

wherein R and the ring A' have the same definitions as above, provided that the pyridine ring represented by the ring A' has no substituent, can be produced in the same manner as with such a compound wherein the pyridine ring has a substituent.

Provided that any of $R^1$, $R^2$, $R^3$, $R^4$, $R^5$ and $R^6$ is a substituent having a free carboxyl group (e.g., carboxylic acid, acetic acid, propionic acid), compound (I) can be converted to the corresponding amide derivative by reaction with an amine derivative which may be substituted or a salt thereof. This reaction can be carried out by a known method. For example, a reactive derivative of compound (I), such as one reactive with acid anhydride, acid chloride, imidazolide or diethylphosphocyanide, is reacted with an amine derivative or a salt thereof. Of these methods, the most convenient is the use of acid chloride. The reaction is preferably carried out in a common solvent (e.g., dichloromethane, chloroform, ethyl acetate, tetrahydrofuran, water, or a mixture thereof) in the presence of a base (e.g., triethylamine, N-methylmorpholine, sodium hydrogen carbonate, potassium carbonate). Reaction temperature is about $-50°$ to $100°$ C., and reaction time is about 0.1 to 10 hours. The amount of amine derivative or salt thereof used is 1 to 2 mol per mol of compound (I).

Provided that any of $R^1$, $R^2$, $R^3$, $R^4$, $R^5$ and $R^6$ is a substituent having a free hydroxyl group (e.g., hydroxymethyl, hydroxyethyl, hydroxypropyl), compound (I) can be converted to the corresponding ester derivative by reaction with a carboxylic acid derivative. This reaction can be carried out by a known method. Such methods include the method wherein compound (I) and a carboxylic acid derivative are directly condensed together in the presence of a condensing agent such as dicyclohexylcarbodiimide, and the method wherein compound (I) and a reactive derivative of carboxylic acid derivative, such as acid anhydride, acid chloride or imidazolide are reacted. Of these methods, the most convenient is the use of acid anhydride or acid chloride. When using an acid anhydride, the reaction is preferably carried out in a common solvent (e.g., dichloromethane, chloroform, ethyl acetate, tetrahydrofuran, water, or a mixture thereof) in the presence of a base (e.g., triethylamine, N-methylmorpholine, sodium hydrogen carbonate, potassium carbonate). Pyridine may be used both as a solvent and as a base. When using an acid chloride, the reaction is preferably carried out in a common solvent (e.g., dichloromethane, chloroform, ethyl acetate, tetrahydrofuran, water, or a mixture thereof) in the presence of a base (e.g., triethylamine, N-methylmorpholine, sodium hydrogen carbonate, potassium carbonate). For all these reactions, reaction temperature is about $-50°$ to $100°$ C., and reaction time is about 0.1 to 10 hours. The amount of acid anhydride or acid chloride used is 1 to 2 mol per mol of compound (I).

A compound represented by formula (II) is produced by reaction of a compound represented by the following formula (III):

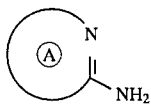

wherein the ring A has the same definition as above, and a compound represented by the following formula (IV):

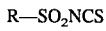

wherein R has the same definition as above.

This reaction is normally carried out in an inert solvent. Examples of such solvents include aromatic hydrocarbons such as benzene, toluene and xylene, hydrocarbon halides such as dichloromethane, chloroform and carbon tetrachloride, ethers such as ethyl ether, dioxane and tetrahydrofuran, nitriles such as acetonitrile and propionitrile, esters such as ethyl acetate, ketones such as acetone and 2-butanone, and amides such as N, N-dimethylformamide. These solvents may be used singly or in combination in any ratio as necessary.

Reaction temperature can be chosen over the range of from about $0°$ to $200°$ C., being preferably about $10°$ to $100°$ C. Reaction time is normally about 0.1 to 50 hours, preferably 0.2 to 5 hours. The amount of compound (IV) used is 1 to 3 mol per mol of compound (III).

A compound represented by formula (IV) can be produced by heating a compound represented by the following formula (V):

R—SO₂NHCS₂R'  (V)

wherein R has the same definition as above, and R' represents a lower alkyl group, at 130° to 180° C. in a high boiling solvent such as xylene or o-chlorobenzene for about 1 to 4 hours.

A compound represented by formula (II) can also be produced by heating compound (III) and compound (V) at 130° to 180° C. in a high boiling solvent such as xylene or o-chlorobenzene for about 1 to 4 hours.

A compound represented by formula (II) can also be produced-by reaction of a compound represented by the following formula (VI):

wherein the ring A has the same definition as above, and a compound represented by the following formula (VII):

R—SO₂NH₂  (VII)

wherein R has the same definition as above, in an inert solvent (e.g., benzene, toluene, xylene, dioxane, N,N-dimethylformamide, or a mixture thereof) in the presence of a base (e.g. triethylamine, N-methylmorpholine, sodium hydrogen carbonate, potassium carbonate).

Compounds represented by formula (I) or (II) thus produced can be isolated and purified by known means of fractional purification such as concentration, concentration under reduced pressure, solvent extraction, crystallization, recrystallization, re-dissolution and chromatography.

Compound (III), used for these production methods can be produced by, or in accordance with, the methods described in Chemical Abstracts, 53, 14089e (1959), Chemical Abstracts, 105, 221003s (1986), European Journal of Medicinal Chemistry, 16, 355 (1981), and *Shin Jikken Kagaku Koza*, 14, "*Yuki Kagobutsu no Gosei to Hanno IV*" (1978), for instance. Compound (V) can be produced by, or in accordance with, the method described in Chemische Berichte, 99, 2885 (1966), for instance.

Compound (VI) can be produced by, or in accordance with, the method described in Organic Synthesis Collective Volume III, 735 (1955), for instance. Compound (VII) can be produced by, or in accordance with, the method described in the Journal of Organic Chemistry 28, 3537 (1963) and Chemical Abstracts, 74, 22502v (1971), for instance.

Since the compound represented by formula (I') or a pharmaceutically acceptable salt thereof exhibits endothelin antagonistic action, it can be used as a pharmaceutical for mammals (e.g., humans, mice, rats, cats, dogs, rabbits, bovines, swine) to treat and prevent various diseases caused by endothelin. For example, said compound can be used as a vasodilator to treat hypertension such as peripheral circulatory failure, heart diseases such as angina pectoris, myocardosis, arteriosclerosis and myocardial infarction, Raynaud's syndrome, cerebral vascular spasm, cerebral ischemia, cerebral apoplectic attacks such as late cerebral vascular spasm following subarachnoid bleeding, bronchial asthma, acute renal failure and endotoxin shock, or a therapeutic drug for chronic nephritis.

Since the compound represented by the formula (I') or a pharmaceutically acceptable salt thereof exhibits excellent bone resorption inhibitory action, as well as potent cathepsin B inhibiting action, it can be used as a pharmaceutical for mammals (e.g., humans, mice, rats, cats, dogs, rabbits, bovines, swine) to treat and prevent diseases involving accentuated bone resorption and diseases caused by accentuated cathepsin B activity such as chronic rheumatoid arthritis and metabolic bone diseases.

The compound represented by formula (I') or a pharmaceutically acceptable salt thereof can be administered orally or parenterally in the form of solid preparations such as tablets, capsules, granules and powders or liquid preparations such as syrups and injections, in pharmaceutically acceptable carriers.

Pharmaceutically acceptable carriers are various organic or inorganic carrier materials commonly used as preparation materials, which are formulated as excipients, lubricants, binders and disintegrating agents in solid preparations, or as solvents, dissolution aids, suspending agents, isotonizing agents, buffers and analgesics in liquid preparations. Also, preparation additives such as preservatives, antioxidants, coloring agents and sweeteners may be used as necessary. Preferable excipients include lactose, sucrose, D-mannitol, starch, crystalline cellulose and light silicic anhydride. Preferable lubricants include magnesium stearate, calcium stearate, talc and colloidal silica. Preferable binders include binding cellulose, sucrose, D-mannitol, dextrin, hydroxypropyl cellulose, hydroxypropylmethyl cellulose and polyvinylpyrrolidone. Preferable disintegrating agents include starch, carboxymethyl cellulose, carboxymethyl cellulose calcium, sucrose calmelose sodium and carboxymethyl starch sodium. Preferable solvents include water for injection, alcohol, propylene glycol, macrogol, sesame oil and corn oil. Preferable dissolution aids include polyethylene glycol, propylene glycol, D-mannitol, benzyl benzoate, ethanol, tris-aminomethane, cholesterol, triethanolamine, sodium carbonate and sodium citrate. Preferable suspending agents include surfactants such as stearyltriethanolamine, sodium lauryl sulfate, laurylaminopropionic acid, lecithin, benzalkonium chloride, benzethonium chlorine and glycerol monostearate, and hydrophilic polymers such as polyvinyl alcohol, polyvinylpyrrolidone, carboxymethyl cellulose sodium, methyl cellulose, hydroxymethyl cellulose, hydroxyethyl cellulose and hydroxypropyl cellulose. Preferable isotonizing agents include sodium chloride, glycerol and D-mannitol. Preferable buffers include phosphate, acetate, carbonate and citrate buffers. Preferable analgesics benzyl alcohol. Preferable preservatives include p-oxybenzoates, chlorobutanol, benzyl alcohol, phenethyl alcohol, dehydroacetic acid and sorbic acid. Preferable antioxidants include sulfites and ascorbic acid.

The compound represented by formula (I') or a pharmaceutically acceptable salt thereof can be used safely with low toxicity (no deaths occurred in mice given a 300 mg/kg dose of the compound obtained in Example 83 below). Although the daily dose varies depending on the condition and weight of the patient, kind of the compound, route of administration and other factors, it is administered parenterally, specifically subcutaneously, intravenously, intramuscularly or rectally at about 0.05 to 100 mg/kg/day, preferably 0.5 to 50 mg/kg/day as an endothelin receptor antagonist, about 0.1 to 100 mg/kg/day, preferably 1 to 50 mg/kg/day as a cathepsin B inhibitor and about 1 to 200 mg/kg/day, preferably 5 to 100 mg/kg/day as a bone resorption suppressor, respectively. For use as an oral agent, it is desirable to administer it at about 0.1 to 500 mg/kg/day, preferably 0.5 to 200 mg/kg/day as an endothelin receptor antagonist, about 1 to 500 mg/kg/day, preferably 10 to 300 mg/kg/day as a cathepsin B inhibitor and about 5 to 1000 mg/kg/day, preferably 10 to 300 mg/kg/day as a bone resorption suppressor, respectively.

The bioactivities of the compound represented by formula (I) or pharmaceutically acceptable salts thereof are described below.

Test 1

Inhibition of endothelin-1 binding to endothelin receptor (a) Preparation of rabbit ventricular microsomal fraction Rabbit ventricular microsomal fraction was prepared by the method described in Methods in Enzymology, 109, 513 with a slight modification. The cardiac ventricular muscle excised from a 2 to 2.5 kg rabbit was minced in solution A (20 mM $NaHCO_3$, 0.1 mM phenylmethylsulfonyl fluoride (PMSF)) and then homogenized using a Polytron PT-20, and centrifuged at 1500×g for 15 minutes. The supernatant was centrifuged at 45000×g for 15 minutes. The resulting sediment was suspended in solution B (50 mM Tris-HCl pH 7.4, 0.1 mM PMSF) and then re-centrifuged at 45000×g for 15 minutes. The sediment was again suspended in solution B and then centrifuged at 45000×g for 15 minutes. The sediment was re-suspended in solution B, and the suspension was frozen with liquid nitrogen and stored at −80° C. This series of operations was performed at 4° C. Protein contents was determined by Lowry's method.

(b) $^{125}$I-endothelin binding test

To 250 μl of a reaction solution (50 mM Tris-HCl, pH 7.4, 0.2% BSA (bovine serum albumin)), supplemented with $6\times10^{-11}$M $^{125}$I-endothelin-1 (Amersham Japan) 50 μl of the ventricular microsomal fraction (20 μg) and a sample were added, followed by incubation at 37° C. for 90 minutes. The reaction mixture was then filtered through a GF/B glass filter (Millipore Japan), and the filter was washed with a 40-fold (12 ml) of the reaction solution. The radioactivity of the $^{125}$I-endothelin on the glass filter was determined using a gamma-ray counter. Nonspecific binding was defined as the amount of $^{125}$I-endothelin in the presence of $4\times10^{-7}$M unlabelled endothelin-1 and was less than 8% of total binding. The specific binding was calculated as total binding minus nonspecific binding. Non-specific binding accounted for not higher than 8% of the total binding. The inhibitory rate of the compound is expressed as the concentration ($IC_{50}$M) required to cause a 50% reduction in the specific binding. The results are given in Table 1.

TABLE 1

| Test Compound | $IC_{50}$ value (M) |
| --- | --- |
| 12 | $6.5 \times 10^{-6}$ |
| 13 | $5.9 \times 10^{-6}$ |
| 14 | $8.8 \times 10^{-6}$ |
| 20 | $3.0 \times 10^{-6}$ |
| 23 | $2.5 \times 10^{-6}$ |
| 24 | $2.5 \times 10^{-6}$ |
| 26 | $4.0 \times 10^{-6}$ |
| 73 | $7.3 \times 10^{-6}$ |
| 82 | $7.5 \times 10^{-6}$ |
| 83 | $6.0 \times 10^{-6}$ |
| 99 | $2.1 \times 10^{-6}$ |
| 104 | $2.7 \times 10^{-6}$ |
| 106 | $4.2 \times 10^{-6}$ |
| 111 | $6.1 \times 10^{-6}$ |
| 112 | $5.2 \times 10^{-6}$ |
| 114 | $3.8 \times 10^{-6}$ |

Note: The above test compound numbers correspond to Examples below.

Test 2

Inhibitory action on endothelin-1-induced constriction in swine coronary artery After fat tissue removal, the swine left coronary arterial anterior descending branch (LAD) was isolated and vascular rings were prepared. These arterial rings kept at 37° C., were suspended in a 20 ml organ chamber filled with Krebs solution being aerated with 95% $O_2$/5% $CO_2$ gas. Two grams of the tension was applied. After equilibration for 1 hr, 60 mMKCl was applied to condition the coronary rings. The test compound was tested for inhibition of the constriction induced by endothelin-1 ($3\times10^{-9}$M) by adding the test compound when the maximum of endothelin-1 induced constriction was reached. Activity is expressed as percent relaxation of the maximum constriction induced by endothelin-1. The results are given in Table 2. The developed tension of rings was reached isometrically.

TABLE 2

| Test compound | % Relaxation | | |
| --- | --- | --- | --- |
| Concentration (M): | $1 \times 10^{-5}$ | $3 \times 10^{-5}$ | $1 \times 10^{-4}$ |
| 12 | 14 | — | 62 |
| 13 | 56 | — | 78 |
| 20 | 11 | — | 68 |
| 24 | 37 | — | 99 |
| 111 | 40 | 78 | — |
| 112 | 35 | 83 | — |
| 114 | 44 | 75 | — |

Note: The above test compound numbers correspond to Examples below.

The results from the above bioassays demonstrate that the compound represented by formula (I) or the salts thereof exhibits endothelin-1 antagonistic action.

Test 3

Determination of cathepsin B inhibitory activity

Cathepsin B (produced by Sigma) was diluted with 100 mM sodium acetate buffer (pH 5.5) to a concentration of 30 μg/ml. To 1 μl of this enzyme dilution, 46 μl of diluent, 2 μl of 0.1M DTT and 25 μl of activator/buffer (340 mM sodium acetate, 60 mM acetic acid, 4 mM EDTA disodium salt, pH 5.5) were added. To this mixture, a 1 μl sample, diluted to $10^{-3}$M with dimethylsulfoxide (DMSO), and 25 μl of 20 μM Z-Phe-Arg-NH-Mec (enzyme substrate solution) were added. After the mixture was incubated at 37° C. for 20 minutes, 100 μl of a stop solution (100 mM sodium monochloroacetate, 30 mM sodium acetate, pH 4.3) was added. The reaction was carried out on a 96-well fluoropiate (produced by Labo-Systems).

After the reaction was stopped, the absorbance of free aminomethylcoumarin was determined by excitation at 365 nm and emission at 450 nm, using Fluorescence Concentration Analyzer (produced by Baxter). One μl of sample-free DMSO was added for control, and the absorbance from reaction of this control was defined as 100% activity. For samples of under 10% residual activity, further dilutions were assayed for residual activity as described above to obtain the $IC_{50}$ value. The results are given in Table 3.

TABLE 3

| Compound (Example No.) | Cathepsin B Inhibitory Activity [$IC_{50}$ (M)] |
| --- | --- |
| 25 | $1.2 \times 10^{-6}$ |
| 31 | $2.9 \times 10^{-6}$ |
| 34 | $9.3 \times 10^{-6}$ |
| 96 | $1.9 \times 10^{-6}$ |
| 98 | $3.5 \times 10^{-6}$ |
| 108 | $1.1 \times 10^{-6}$ |

Test 4

Inhibition of bone resorption

The inhibitory effect of compound on bone resorption was measured by the method of Rais 3 [Journal of Clinical Investigation, 44, 103–116 (1965)]. Specifically, one Sprague-Dawley rat, at 19 days of gestation, was given 50 μCi of $^{45}Ca$ (calcium isotope, in $CaCl_2$ solution) by subcutaneous injection. On the following day, fetal rats were aseptically taken out, both forearm bones (radius and ulna) were cut out from the body of each fetus, and connective tissue and cartilages were removed to maximum possible extent, to yield prepare bone culture samples. Each bone fragment was incubated at 37° C. for 24 hours in 0.6 ml of $BGJ_b$ medium (Fitton-Jackson modification, produced by GIBCO Laboratories, United States) containing 2 mg/ml bovine serum albumin, after which it was cultured in the same medium as above but containing a 10 μg/ml compound for two more days. $^{45}Ca$ radioactivity in the medium and $^{45}Ca$ radioactivity in the bone were then measured, and the percent ratio of $^{45}Ca$ released from the bone to the medium was calculated using the following equation:

$$\text{Percent ratio of } ^{45}Ca \text{ released from bone to medium (\%)} = \frac{^{45}Ca \text{ count in the medium}}{(^{45}Ca \text{ count in the medium}) + (^{45}Ca \text{ count in the bone})} \times 100$$

For control, bone fractions from fetuses of the same litter were cultured for two days in the absence of the test compound. The mean ± standard deviation for the values from five bone fragments in each group were calculated, and their percent ratios to the control were calculated. The results are given in Table 4.

TABLE 4

| Compound (Example No.) | Inhibition of Bone Resorption [$^{45}Ca$ released (percent ratio to control)] |
|---|---|
| 25 | 72 |
| 34 | 75 |
| 65 | 74 |
| 94 | 76 |
| 96 | 81 |
| 98 | 87 |
| 108 | 85 |
| 111 | 75 |
| 115 | 85 |

EXAMPLES

The present invention is hereinafter described in more detail by means of the following reference examples and working examples, which are not to be construed as limitative. Figures for melting point were obtained by the hot plate method and remain uncorrected.

In the description below, Me, Et, Ph, Bz and Ac represent a methyl group, an ethyl group, a phenyl group, a benzyl group and an acetyl group, respectively.

Reference Example 1

A mixture of methyl 4-methylphenylsulfonyldithiocarbamate (2.60 g) and xylene (20 ml) was refluxed with heating for 4.5 hours. After solvent removal, the residue was dissolved in acetone (20 ml), and 2-amino-4,6-dimethylpyridine (1.22 g) was added, followed by stirring at room temperature for 30 minutes. The separating crystal was collected by filtration and recrystallized from ethyl acetate-chloroform-methanol to yield 1-(4,6-dimethyl-2-pyridyl)-3-(4-methylphenyl)sulfonyl-2-thio urea (2.96 g, yield 88%) as a light yellow needle.

Melting point: 167° to 168° C. (decomposed)

Elemental analysis (for $C_{15}H_{17}N_3O_2S_2$): Calculated (%): C, 53.71; H, 5.11; N, 12.53 Found (%): C, 53.49; H, 5.09; N, 12.29.

Reference Examples 2 through 78

The compounds listed in Tables 5 through 12 were obtained in the same manner as in Reference Example 1.

TABLE 5

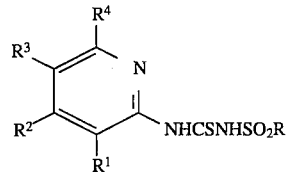

| Reference Example | $R^1$ | $R^2$ | $R^3$ | $R^4$ | R | Yield (%) | mp (°C.) | Recrystallizing Solvent |
|---|---|---|---|---|---|---|---|---|
| 2 | H | Me | H | Me | Me-Ph | 80 | 151–152 | Dichloromethane-isopropyl ether |
| 3 | H | Me | H | Me | Ph | 96 | 156–157 | Dichloromethane-isopropyl ether |

TABLE 5-continued

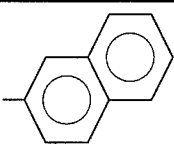

| Reference Example | R¹ | R² | R³ | R⁴ | R | Yield (%) | mp (°C.) | Recrystallizing Solvent |
|---|---|---|---|---|---|---|---|---|
| 4 | H | Me | H | Me | 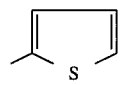 | 82 | 166–167 | Dichloromethane-ethanol |
| 5 | H | Me | H | Me | 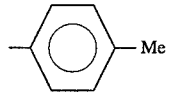 | 72 | 153–155 | Dichloromethane-ethanol |
| 6 | H | Me | H | Me | Et | 67 | 158–159 | Dichloromethane-ethanol |
| 7 | H | H | Cl | H | 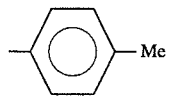 | 86 | Note 1) 180–181 | Acetone-ethyl acetate |
| 8 | OCH₂Ph | H | H | H | 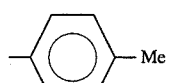 | 94 | 143–144 | Dichloromethane-isopropyl ether |
| 9 | OH | H | H | H | 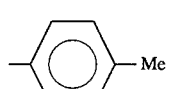 | 92 | 145–146 | Methanol-ethyl acetate |
| 10 | H | H | —(CH₂)₄— | | 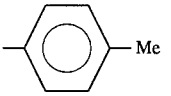 | 79 | Note 1) 181–182 | Chloroform-methanol |

TABLE 6

| Reference Example | R¹ | R² | R³ | R⁴ | R | Yield (%) | mp (°C.) | Recrystallizing Solvent |
|---|---|---|---|---|---|---|---|---|
| 11 | —(CH₂)₄— | | H | H | 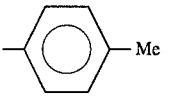 | 72 | 144–145 | Ethyl acetate |
| 12 | H | —(CH₂)₄— | | H | 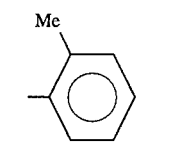 | 63 | Note 1) 167–168 | Ethyl acetate |
| 13 | H | —(CH₂)₄— | | H | Me  | 83 | 160–161 | Dichloromethane-isopropyl ether |
| 14 | H | —(CH₂)₄— | | H | | 83 | 159–160 | Dichloromethane-isopropyl ether |

TABLE 6-continued

| Reference Example | R¹ | R² | R³ | R⁴ | R | Yield (%) | mp (°C.) | Recrystallizing Solvent |
|---|---|---|---|---|---|---|---|---|
| 15 | H | —(CH$_2$)$_4$— | | H | Me | 85 | Note 1) 177–178 | Dichloromethane-methanol |
| 16 | H | —(CH$_2$)$_4$— | | H | Et | 80 | 164–165 | Dichloromethane-ethanol |
| 17 | —(CH=CH)$_2$— | | H | H | 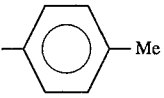—Me | 51 | 162–163 | Chloroform-methanol |
| 18 | H | —(CH=CH)$_2$— | | H | 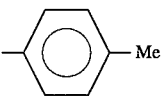—Me | 59 | Note 1) 183–184 | Chloroform-methanol |
| 19 | H | H | —(CH=CH)$_2$— | | 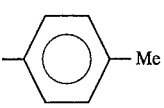—Me | 76 | Note 1) 177–178 | Chloroform-methanol |

1) Decomposed.

TABLE 7

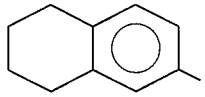

| Reference Example | R⁵ | R⁶ | R | Yield (%) | mp (°C.) | Recrystallizing Solvent |
|---|---|---|---|---|---|---|
| 20 | 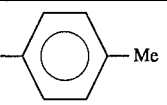 | H | 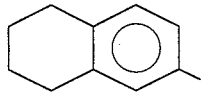—Me | 59 | 189–190 | Dichloromethane-ethanol |
| 21 | 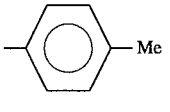 | Me | 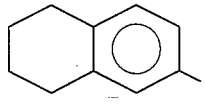—Me | 99 | 179–180 | Dichloromethane-isopropy ether |
| 22 |  | Et | 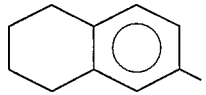—Me | 89 | 177–178 | Dichloromethane-ethanol |
| 23 | 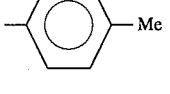 | $^n$C$_3$H$_7$ | 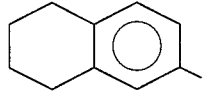—Me | 93 | 177–178 | Dichloromethane-methanol |
| 24 | 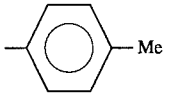 | CH(Me)$_2$ | 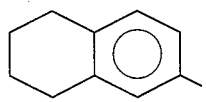—Me | 73 | 185–186 | Dichloromethane-methanol |
| 25 | 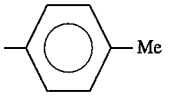 | CH$_2$—⌬—H | 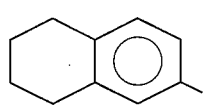—Me | 78 | 124–126 | Dichloromethane-ethanol |
| 26 | 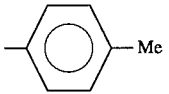 | CH$_2$CO$_2$Et | —◯—Me | 84 | 170–171 | Dichloromethane-ethanol |

TABLE 7-continued

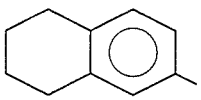

| Reference Example | R⁵ | R⁶ | R | Yield (%) | mp (°C.) | Recrystallizing Solvent |
|---|---|---|---|---|---|---|
| 27 | 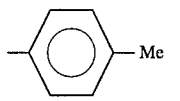 | CH₂CO₂CH₂Ph | 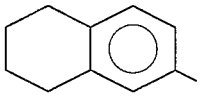—Me | 74 | 191–192 | Dichloromethane-methanol |
| 28 | 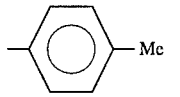 | Ph | 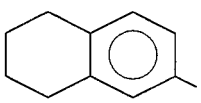—Me | 83 | 185–186 | Dichloromethane-ethanol |
| 29 | 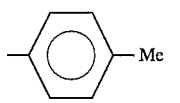 | Br | 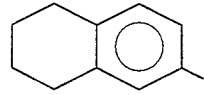—Me | 26 | Note 1) 218–220 | Acetone-methanol |

TABLE 8

| Reference Example | R⁵ | R⁶ | R | Yield (%) | mp (°C.) | Recrystallizing Solvent |
|---|---|---|---|---|---|---|
| 30 | 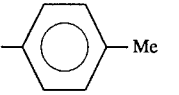 | CH₂CONHMe₂ | 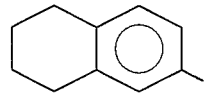—Me | 87 | 178–179 | Dichloromethane-methanol |
| 31 | 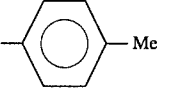 | CH₂CONHEt | 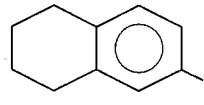—Me | 87 | 191–192 | Dichloromethane-methanol |
| 32 | 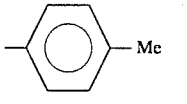 | CH₂CONHCH₂Ph | 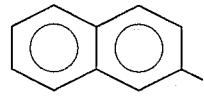—Me | 81 | 130–132 | Methanol-diethyl ether |
| 33 | 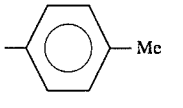 | Et | 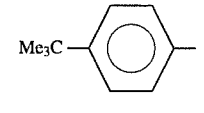—Me | 98 | 133–134 | Dichloromethane-isopropyl ether |
| 34 | Me₃C—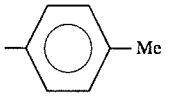— | H | 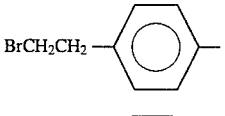—Me | 56 | 195–196 | Dichloromethane-ethanol |
| 35 | BrCH₂CH₂—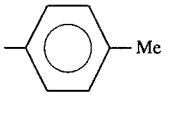— | Me | 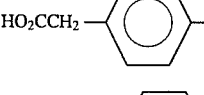—Me | 74 | 149–150 | Dichloromethane-ethanol |
| 36 | HO₂CCH₂—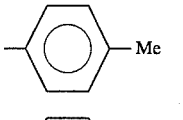— | Me | 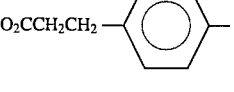—Me | 86 | 154–155 | Methanol-ethyl acetate |
| 37 | HO₂CCH₂CH₂—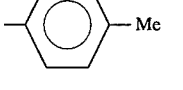— | Me | —Me | 67 | 165–166 | Acetone-isopropyl ether |

TABLE 8-continued

| Reference Example | R⁵ | R⁶ | R | Yield (%) | mp (°C.) | Recrystallizing Solvent |
|---|---|---|---|---|---|---|
| 38 | NHCH₂CO₂Et–COCH₂CH₂–C₆H₄– | Me | –C₆H₄–Me | 91 | 154–155 | Dichloromethane-ethanol |
| 39 | Cl–C₆H₄–CH₂O–C₆H₄– | Me | –C₆H₄–Me | 98 | 181–182 | Dichloromethane-ethanol |
| 40 | Ph, MeO–C₆H₃– | Me | –C₆H₄–Me | 92 | 126–127 | Dichloromethane-ethanol |
| 41 | Ph–O–C₆H₄– | Me | –C₆H₄–Me | 83 | Note 1) 190–191 | Dichloromethane-ethanol |

TABLE 9

| Reference Example | R⁵ | R⁶ | R | Yield (%) | mp (°C.) | Recrystallizing Solvent |
|---|---|---|---|---|---|---|
| 42 | Ph–S–C₆H₄– | Me | –C₆H₄–Me | 70 | 200–201 | Dichloromethane-ethanol |
| 43 | Ph–SO–C₆H₄– | Me | –C₆H₄–Me | 66 | 184–185 | Dichloromethane-ethanol |
| 44 | Ph–C₆H₄– | H | –C₆H₄–Me | 86 | Note 1) 194–195 | Dichloromethane-ethanol |
| 45 | Ph–C₆H₄– | Me | –C₆H₄–Me | 76 | Note 1) 193–195 | Dichloromethane-ethanol |
| 46 | CO₂Me, Ph–C₆H₃– | Me | –C₆H₄–Me | 90 | 161–162 | Dichloromethane-ethanol |
| 47 | Ph– | H | –C₆H₄–Me | 75 | 172–173 | Acetone-isopropyl ether |
| 48 | Ph– | Me | –C₆H₄–Me | 86 | 175–176 | Dichloromethane-ethanol |

TABLE 9-continued

| Reference Example | R⁵ | R⁶ | R | Yield (%) | mp (°C.) | Recrystallizing Solvent |
|---|---|---|---|---|---|---|
| 49 | 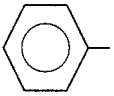 | CO₂Et | 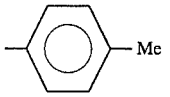Me | 46 | 183–184 | Dichloromethane-ethanol |
| 50 | Me | H | 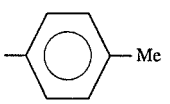Me | 77 | Note 1) 182–183 | Acetone-isopropyl ether |
| 51 | Me | Me | 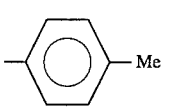Me | 92 | 171–172 | Dichloromethane-ethanol |
| 52 | Me | CO₂Et | 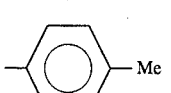Me | 73 | 174–175 | Dichloromethane-methanol |
| 53 | —(CH₂)₄— | | 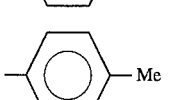Me | 69 | Note 1) 188–190 | Chloroform-methanol |

TABLE 10

| Reference Example | R⁵ | R⁶ | R | Yield (%) | mp (°C.) | Recrystallizing Solvent |
|---|---|---|---|---|---|---|
| 54 | —CH=CH—CH=CH— | | 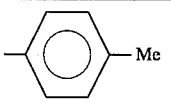Me | 54 | 181–182 | Chloroform-ethanol |
| 55 | 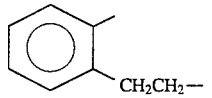CH₂CH₂— | | 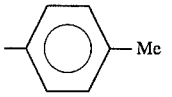Me | 86 | 182–183 | Dichloromethane-ethanol |
| 56 | EtO₂CCH₂ | H | 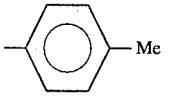Me | 79 | 193–194 | Dichloromethane-ethanol |
| 57 | EtO₂CCH₂ | Me | 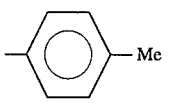Me | 71 | 169–170 | Acetone-isopropyl ether |
| 58 | EtO₂CCH₂ | Et | 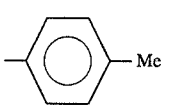Me | 89 | 167–168 | Dichloromethane-ethanol |
| 59 | HO₂CCH₂ | H | 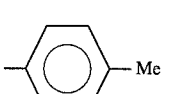Me | 38 | 171–172 | Chloroform-methanol |
| 60 | 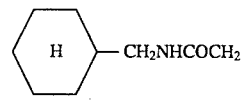—CH₂NHCOCH₂ | Me | 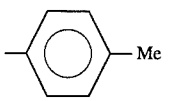Me | 47 | 174–176 | Ethanol-diethyl ether |

TABLE 10-continued

| Reference Example | R⁵ | R⁶ | R | Yield (%) | mp (°C.) | Recrystallizing Solvent |
|---|---|---|---|---|---|---|
| 61 | (cyclohexyl, H)—CH₂NHCOCH₂ | Et | (phenyl)—Me | 59 | 142–143 | Dichloromethane-isopropyl ether |
| 62 | PhCH₂NHCOCH₂ | H | (phenyl)—Me | 67 | 116–117 | Dichloromethane-diethyl ether |
| 63 | (morpholino) O\_\_\_NCOCH₂ | H | (phenyl)—Me | 80 | 186–187 | Chloroform |
| 64 | P(O)(OEt)₂—CH₂—(phenyl)—NHCOCH₂ | H | (phenyl)—Me | 68 | 185–186 | Acetone-diethyl ether |
| 65 | (tetrahydronaphthyl)—NHCOCH₂ | Et | (phenyl)—Me | 80 | 153–154 | Methanol-ethyl acetate |

TABLE 11

| Reference Example | R⁵ | R⁶ | R | Yield (%) | mp (°C.) | Recrystallizing Solvent |
|---|---|---|---|---|---|---|
| 66 | (cyclohexyl-H)—(phenyl)— | H | (phenyl)—Me | 84 | Note 1) 201–202 | Chloroform-ethyl acetate |
| 67 | (cyclohexyl-H)—(phenyl)— | Me | (phenyl)—Me | 91 | 193–194 | Dichloromethane-ethanol |
| 68 | (cyclohexyl-H)—(phenyl)— | Me | Me—(phenyl) | 100 | 206–207 | Chloroform-methanol |
| 69 | (cyclohexyl-H)—(phenyl)— | Me | (phenyl) | 96 | 198–199 | Dichloromethane-isopropyl ether |
| 70 | (cyclohexyl-H)—(phenyl)— | Me | Me—(phenyl)—Me, Me | 89 | 175–176 | Dichloromethane-isopropyl ether |

TABLE 11-continued

| Reference Example | R⁵ | R⁶ | R | Yield (%) | mp (°C.) | Recrystallizing Solvent |
|---|---|---|---|---|---|---|
| 71 | cyclohexyl-phenyl (H) | Me | 2,4,6-triisopropylphenyl (Me₂CH, CHMe₂, Me₂CH) | 77 | 175–176 | Dichloromethane-methanol |
| 72 | cyclohexyl-phenyl (H) | Me | 4-(NHCOMe)phenyl | 82 | 168–169 | Dichloromethane-methanol |
| 73 | cyclohexyl-phenyl (H) | Me | naphthyl | 86 | 177–178 | Dichloromethane-ethanol |
| 74 | cyclohexyl-phenyl (H) | Me | naphthyl | 68 | 194–195 | Dichloromethane-ethanol |
| 75 | cyclohexyl-phenyl (H) | Me | 2-methylthiophene (S) | 87 | Note 1) 173–174 | Dichloromethane-ethanol |

TABLE 12

| Reference Example | R⁵ | R⁶ | R | Yield (%) | mp(°C.) | Recrystallizing Solvent |
|---|---|---|---|---|---|---|
| 76 | cyclohexyl-phenyl (H) | Me | Me | 92 | 216–218 | Dichloromethane-methanol |
| 77 | cyclohexyl-phenyl (H) | Me | Et | 98 | Note 1) 182–183 | Dichloromethane-ethanol |
| 78 | cyclohexyl-phenyl (H) | Me | CH₂Ph | 72 | 124–125 | Dichloromethane-ethanol |

1) Decomposed.

Example 1

To a mixture of 1-(4,6-dimethyl-2-pyridyl)-3-(4-methylphenyl) sulfonyl-2-thiourea (2.90 g) and chloroform (50 ml), sulfuryl chloride (1.28 g) was added. After being stirred at room temperature for 15 minutes, the mixture was refluxed with heating for 30 minutes. The reaction mixture was concentrated, and the resulting crystal was collected by filtration and suspended in water. After pH adjustment to 7 by the addition of saturated aqueous sodium bicarbonate, the suspension was stirred at room temperature for 1 hour. The separating crystal was collected by filtration and recrystallized from chloroform-methanol to yield 5, 7-dimethyl-2-(4-methylphenyl) sulfonylimino-2H-[1,2,4]thiadiazolo[2, 3-a]pyridine (2.40 g, yield 83%) as a colorless needle.

Melting point: 228° to 229° C. (decomposed)

Elemental analysis (for $C_{15}H_{15}N_3O_2S_2$): Calculated (%): C, 54.03; H, 4.53; N, 12.60 Found (%): C, 54.00; H, 4.50; N, 12.40.

Examples 2 through 19

The compounds listed in Tables 13 and 14 were obtained in the same manner as in Example 1.

TABLE 13

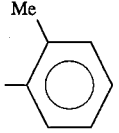

| Example | R¹ | R² | R³ | R⁴ | R | Yield (%) | mp(°C.) | Recrystallizing Solvent |
|---------|------|------|------|------|---|-----------|---------|-------------------------|
| 2 | H | Me | H | Me | 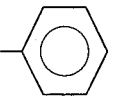 Me (2,3-dimethylphenyl) | 89 | 195–196 | Dichloromethane-ethanol |
| 3 | H | Me | H | Me | 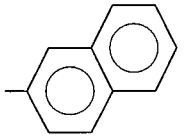 (o-tolyl) | 95 | 203–204 | Dichloromethane-ethanol |
| 4 | H | Me | H | Me | 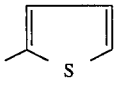 (naphthyl) | 90 | 212–213 | Dichloromethane-ethanol |
| 5 | H | Me | H | Me | 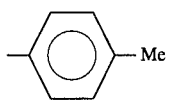 (thienyl) | 78 | 214–215 | Dichloromethane-ethanol |
| 6 | H | Me | H | Me | Et | 72 | 181–182 | Dichloromethane-ethanol |
| 7 | H | H | Cl | H | 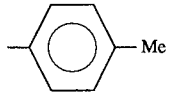—Me | 60 | 243–244 | Dimethylformamide |
| 8 | OCH₂Ph | H | H | H | 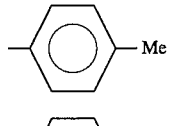—Me | 90 | 219–223 | Dimethylformamide-water |
| 9 | OH | H | H | H | 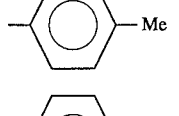—Me | 47 | 267–268 | Dimethylformamide-water |
| 10 | H | H | —(CH₂)₄— | | 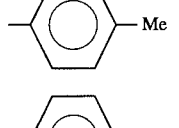—Me | 62 | Note 1) 242–243 | Chloroform-methanol |
| 11 | —(CH₂)₄— | | H | H | —Me | 85 | 221–222 | Dimethylformamide-methanol |
| 12 | H | —(CH₂)₄— | | H | —Me | 94 | Note 1) 205–206 | Chloroform-ethyl acetate |

TABLE 13-continued

| Example | R¹ | R² | R³ | R⁴ | R | Yield (%) | mp(°C.) | Recrystallizing Solvent |
|---|---|---|---|---|---|---|---|---|
| 13 | H | —(CH₂)₄— | | H | Me-phenyl (o-tolyl) | 83 | 198–199 | Dichloromethane-methanol |
| 14 | H | —(CH₂)₄— | | H | phenyl | 94 | 199–200 | Dichloromethane methanol |

TABLE 14

| Example | R¹ | R² | R³ | R⁴ | R | Yield (%) | mp(°C.) | Recrystallizing Solvent |
|---|---|---|---|---|---|---|---|---|
| 15 | H | —(CH₂)₄— | | H | Me | 88 | Note 1) 193–194 | Dichloromethane-methanol |
| 16 | H | —(CH₂)₄— | | H | Et | 55 | 175–176 | Acetone-ethanol |
| 17 | —(CH=CH)₂— | | H | H | phenyl-Me | 84 | Note 1) 280–281 | Dimethylformamide-methanol |
| 18 | H | —(CH=CH)₂— | | H | phenyl-Me | 94 | Note 1) 237–238 | Dimethylformamide-water |
| 19 | H | H | —(CH=CH)₂— | | phenyl-Me | 61 | 240–241 | Chloroform-diethyl ether |

1) Decomposed.

Example 20

To a mixture of 1-[5-ethyl-4-(5,6,7,8-tetrahydro-2-naphthyl)-2-thiazolyl]-3-(4-methylphenyl) sulfonyl-2-thiourea (1.40 g) and chloroform (10 ml), sulfuryl chloride (420 mg) was added. After being stirred at room temperature for 2 hours, the reaction mixture was concentrated; the residue was treated with ethanol, and the resulting crystal was collected by filtration and recrystallized from dichloromethane-ethanol to yield 5-ethyl-2-(4-methylphenyl)sulfonylimino-6-(5,6,7,8-tetrahydro-2-naphthyl)-2H-thiazolo[3,2-b][1,2,4]thiadiazole (1.00 g, yield 72%) as a colorless needle.

Melting point: 151° to 152° C.

Elemental analysis (for $C_{23}H_{23}N_3O_2S_3$): Calculated (%): C, 58.82;H, 4.94;N, 8.95 Found (%): C, 58.85;H, 4.85;N, 8.97.

Examples 21 through 83

The compounds listed in Tables 15 through 20 were obtained in the same manner as in Example 20.

TABLE 15

$$R^5, R^6, S, N_2, S, N^4, NSO_2R \text{ (structure)}$$

| Example | R⁵ | R⁶ | R | Yield (%) | mp(°C.) | Recrystallizing Solvent |
|---|---|---|---|---|---|---|
| 21 | tetrahydronaphthyl | H | 4-Me-phenyl | 36 | 182–183 | Dichloromethane-ethanol |
| 22 | tetrahydronaphthyl | Me | 4-Me-phenyl | 85 | 202–203 | Dichloromethane-isopropyl ether |
| 23 | tetrahydronaphthyl | ⁿC₃H₇ | 4-Me-phenyl | 86 | 153–154 | Dichloromethane-ethanol |
| 24 | tetrahydronaphthyl | CH(Me)₂ | 4-Me-phenyl | 82 | 199–200 | Dichloromethane-ethanol |
| 25 | tetrahydronaphthyl | CH₂-cyclohexyl | 4-Me-phenyl | 86 | 175–176 | Dichloromethane-ethanol |
| 26 | tetrahydronaphthyl | CH₂CO₂Et | 4-Me-phenyl | 86 | 141–142 | Dichloromethane-isopropyl ether |
| 27 | tetrahydronaphthyl | CH₂CO₂CH₂Ph | 4-Me-phenyl | 90 | Note 1) Oily substance | |
| 28 | tetrahydronaphthyl | Ph | 4-Me-phenyl | 82 | 220–221 | Dichloromethane-ethanol |
| 29 | tetrahydronaphthyl | Br | 4-Me-phenyl | 55 | 176–177 | Dichloromethane-methanol |
| 30 | tetrahydronaphthyl | CH₂CONMe₂ | 4-Me-phenyl | 90 | 185–186 | Dichloromethane-methanol |

TABLE 16

| Example | R⁵ | R⁶ | R | Yield (%) | mp(°C.) | Recrystallizing Solvent |
|---|---|---|---|---|---|---|
| 31 | tetrahydronaphthyl | CH₂CONHEt | 4-Me-phenyl | 59 | 178–179 | Acetone-methanol |
| 32 | tetrahydronaphthyl | CH₂CONHCH₂Ph | 4-Me-phenyl | 83 | 146–147 | Dichloromethane-methanol |

TABLE 16-continued

| Example | R⁵ | R⁶ | R | Yield (%) | mp(°C.) | Recrystallizing Solvent |
|---|---|---|---|---|---|---|
| 33 | 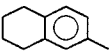 | CH₂CONH——H | —Me | 77 Note 2) | 196–197 | Dichloromethane-methanol |
| 34 | 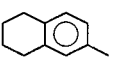 | CH₂CONH——Me | —Me | 56 Note 2) | 204–205 | Dichloromethane-methanol |
| 35 | 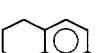 | CH₂CH₂OH | —Me | 52 Note 2) | 156–157 | Dichloromethane-methanol |
| 36 | 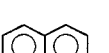 | Et | —Me | 78 | 193–194 | Dichloromethane-isopropyl ether |
| 37 | Me₃C—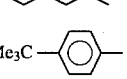— | H | —Me | 74 | 186–187 | Dichloromethane-isopropyl ether |
| 38 | BrCH₂CH₂—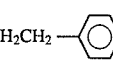— | Me | —Me | 62 | 165–166 | Dichloromethane-ethanol |
| 39 | HO₂CCH₂—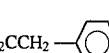— | Me | —Me | 37 | 217–218 | Dichloromethane-methanol |
| 40 | HO₂CCH₂CH₂—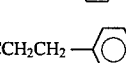— | Me | —Me | 77 | 183–184 | Dichloromethane-ethanol |
| 41 | NHCH₂CO₂Et<br>\|<br>COCH₂CH₂ | Me | 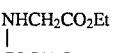—Me | 55 | 151–152 | Ethanol-isopropyl ether |
| 42 | Cl——CH₂O—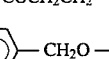— | Me | —Me | 86 | 207–208 | Dichloromethane-isopropyl ether |

TABLE 17

| Example | R⁵ | R⁶ | R | Yield (%) | mp(°C.) | Recrystallizing Solvent |
|---|---|---|---|---|---|---|
| 43 | 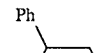 | Me | —Me | 77 | 138–139 | Dichloromethane-ethanol |
| 44 | 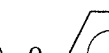 | Me | —Me | 69 | 160–161 | Acetone-methanol |
| 45 |  | Me | —Me | 92 | 202–203 | Dichloromethane-ethanol |
| 46 |  | Me | —Me | 38 | 133–135 | Dichloromethane-ethanol |
| 47 | 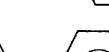 | H | —Me | 80 | 198–199 | Dichloromethane-ethanol |
| 48 | 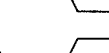 | Me | —Me | 90 | 195–196 | Dichloromethane-ethanol |

TABLE 17-continued

| Example | $R^5$ | $R^6$ | R | Yield (%) | mp(°C.) | Recrystallizing Solvent |
|---|---|---|---|---|---|---|
| 49 | 2-(CO₂Me)-biphenyl-4-yl | Me | 4-Me-C₆H₄- | 87 | 192–193 | Dichloromethane-ethanol |
| 50 | Ph | H | 4-Me-C₆H₄- | 75 | 186–187 | Dichloromethane-isopropyl ether |
| 51 | Ph | Me | 4-Me-C₆H₄- | 92 | 200–201 | Dichloromethane-ethanol |
| 52 | Ph | CO₂Et | 4-Me-C₆H₄- | 78 | 206–207 | Dichloromethane-ethanol |
| 53 | Me | H | 4-Me-C₆H₄- | 57 | 187–188 | Acetone-isopropyl ether |
| 54 | Me | Me | 4-Me-C₆H₄- | 72 | 181–182 | Dichloromethane-ethanol |

TABLE 18

| Example | $R^5$ | $R^6$ | R | Yield (%) | mp(°C.) | Recrystallizing Solvent |
|---|---|---|---|---|---|---|
| 55 | Me | CO₂Et | 4-Me-C₆H₄- | 61 | 178–179 | Dichloromethane-methanol |
| 56 | —(CH₂)₄— | | 4-Me-C₆H₄- | 74 | Note 3) 205–206 | Chloroform-methanol |
| 57 | —CH=CH—CH=CH— | | 4-Me-C₆H₄- | 75 | 218–219 | Dimethylformamide-water |
| 58 | 2-Me-C₆H₄-CH₂CH₂— | | 4-Me-C₆H₄- | 90 | 204–205 | Dichloromethane-isopropyl ether |
| 59 | EtO₂CCH₂ | H | 4-Me-C₆H₄- | 69 | 124–125 | Dichloromethane-ethanol |
| 60 | EtO₂CCH₂ | Me | 4-Me-C₆H₄- | 20 | 133–134 | Acetone-methanol |

TABLE 18-continued

| Example | R⁵ | R⁶ | R | Yield (%) | mp(°C.) | Recrystallizing Solvent |
|---|---|---|---|---|---|---|
| 61 | EtO₂CCH₂ | Et | 4-Me-C₆H₄- | 80 | 100–101 | Dichloromethane-ethanol |
| 62 | HO₂CCH₂ | H | 4-Me-C₆H₄- | 33 | Note 3) 151–152 | Acetone-diethyl ether |
| 63 | C₆H₁₁-CH₂NHCOCH₂ | H | 4-Me-C₆H₄- | Note 2) 24 | 185–186 | Ethanol-diethyl ether |
| 64 | C₆H₁₁-CH₂NHCOCH₂ | Me | 4-Me-C₆H₄- | 47 | 188–189 | Acetone |
| 65 | C₆H₁₁-CH₂NHCOCH₂ | Et | 4-Me-C₆H₄- | 83 | 180–181 | Dichloromethane-ethanol |
| 66 | PhCH₂NHCOCH₂ | H | 4-Me-C₆H₄- | 60 | 160–161 | Ethanol-diethyl ether |

TABLE 19

| Example | R⁵ | R⁶ | R | Yield (%) | mp (°C.) | Recrystallizing Solvent |
|---|---|---|---|---|---|---|
| 67 | morpholino-NCOCH₂ (O in ring) | H | 4-Me-C₆H₄- | 19 | 170–172 | Ethanol-diethyl ether |
| 68 | piperidino-NCOCH₂ | H | 4-Me-C₆H₄- | Note 2) 10 | 157–158 | Chloroform-methanol |
| 69 | (EtO)₂(O)P-CH(−C₆H₄−NHCOCH₂) | H | 4-Me-C₆H₄- | 21 | 160–161 | Chloroform-methanol |
| 70 | 1,2,3,4-tetrahydronaphth-2-yl-NHCOCH₂ | Et | 4-Me-C₆H₄- | 89 | 187–188 | Dichloromethane-ethanol |
| 71 | 4-C₆H₁₁-C₆H₄- | H | 4-Me-C₆H₄- | 73 | 190–191 | Dichloromethane-isopropyl ether |
| 72 | 4-C₆H₁₁-C₆H₄- | Me | 4-Me-C₆H₄- | 94 | 146–147 | Dichloromethane-isopropyl ether |

TABLE 19-continued

| Example | R⁵ | R⁶ | R | Yield (%) | mp (°C.) | Recrystallizing Solvent |
|---|---|---|---|---|---|---|
| 73 | H–⌬–⌬– | Me | Me–C₆H₄– (o-Me) | 59 | 132–133 | Dichloromethane-methanol |
| 74 | H–⌬–⌬– | Me | C₆H₅– | 53 | 135–136 | Dichloromethane-methanol |
| 75 | H–⌬–⌬– | Me | 2,4-Me₂-C₆H₃– | 90 | 199–200 | Dichloromethane-methanol |
| 76 | H–⌬–⌬– | Me | 2,4,6-(Me₂CH)₃-C₆H₂– | 90 | 203–204 | Dichloromethane-methanol |
| 77 | H–⌬–⌬– | Me | 4-NHCOMe-C₆H₄– | 79 | 189–190 | Dichloromethane-methanol |
| 78 | H–⌬–⌬– | Me | 2-naphthyl | 60 | Note 4) Oily substance | |

TABLE 20

| Example | R⁵ | R⁶ | R | Yield (%) | mp (°C.) | Recrystallizing Solvent |
|---|---|---|---|---|---|---|
| 79 | H–⌬–⌬– | Me | 1-naphthyl | 89 | 224–225 | Dichloromethane-ethanol |
| 80 | H–⌬–⌬– | Me | 2-thienyl | 75 | 186–187 | Acetone-ethanol |
| 81 | H–⌬–⌬– | Me | Me | 57 | 203–204 | Dichloromethane-methanol |
| 82 | H–⌬–⌬– | Me | Et | 76 | 163–164 | Dichloromethane-ethanol |

TABLE 20-continued

| Example | R⁵ | R⁶ | R | Yield (%) | mp (°C.) | Recrystallizing Solvent |
|---------|----|----|---|-----------|----------|-------------------------|
| 83 | (cyclohexyl-H)-phenyl- | Me | CH₂Ph | 72 | 178–179 | Dichloromethane-ethanol |

1) NMR (δ in CDCl₃): 1.75–1.95 (4H,m), 2.38 (3H, s), 2.7–2.9 (4H,m), 3.76 (2H, s), 5.19 (2H,s), 7.1–7.5 (5H,m), 7.37 (5H,s), 7.77 (2H,d,J=8.5 Hz). 2) Yield from corresponding aminothiazole. 3) Decomposed. 4) NMR (δ in CDCl₃): 1.2–2.05 (10H,m), 2.42(3H,s), 2.5–2.7 (1H,m), 7.42(4H,s), 7.5–7.65(2H,m), 7.8–8.0 (4H,m), 8.46(1H,s).

Example 84

A mixture of 2-[2-(4-methylphenyl) sulfonylimino-6-(5,6,7,8-tetrahydro-2-naphthyl)- 2H-thiazolo[3,2-b][1,2,4]thiadiazol-5-yl]ethanol (500 mg), acetic anhydride (1 ml) and pyridine (5 ml) was stirred at room temperature for i hour. The reaction mixture was added to water, and the resulting crystal was collected by filtration and washed with water. The obtained crystal was subjected to silica gel chromatography and eluted with ethyl acetate-hexane (1:1, v/v). The separating crystal was recrystallized from dichloromethane-methanol to yield 2-[2-(4-methylphenyl)sulfonylimino-6-(5,6,7,8-tetrahydro-2-naphthyl)-2H-thiazolo[3,2-b][1,2,4]thiadiazol-5-yl]ethyl acetate (355 mg, yield 65%) as a colorless needle.

Melting point: 126° to 127° C.

Elemental analysis (for C₂₅H₂₅N₃O₄S₃): Calculated (%): C, 56.90; H, 4.78; N, 7.96 Found (%): C, 56.69; H, 4.78; N, 7.95.

Example 85

3-[4-(5-Methyl-2-(4-methylphenyl)sulfonylimino-2H-thiazolo[3,2-b][1,2,4]thiadiazol- 6-yl]phenyl]propionic acid (500 mg) was dissolved in tetrahydrofuran (10 ml). To this solution were added dimethylformamide (one drop) and oxalyl chloride (160 mg) at room temperature. After mixture stirring for 2 hours, the solvent was distilled off. The residue was dissolved in dichloromethane (10 ml), and a solution of 3,4-(dimethoxy) aniline (165 mg) and triethylamine (110 mg) in dichloromethane (5 ml) was added. After stirring at room temperature for 1 hour, the reaction mixture was washed with 2N hydrochloric acid and water, and dried (magnesium sulfate), after which the solvent was distilled off. The residue was subjected to silica gel chromatography and eluted with ethyl acetate-chloroform (1:1, v/v) to yield a crystal of N-(3,4-dimethoxyphenyl)- 3-[4-[5-methyl-2-(4-methylphenyl) sulfonylimino-2H-thiazolo[3,2-b][1,2,4]thiadiazol-6-yl]phenyl]propionamide (425 mg, yield 65%). This product was recrystallized from dichloromethane-ethanol to yield a colorless prismatic crystal.

Melting point: 203° to 204° C.

Elemental analysis (for C₂₉H₂₈N₄O₅S₃0.5H₂O): Calculated (%): C, 56.38; H, 4.73; N, 9.07 Found (%): C, 56.42; H, 4.75; N, 8.95.

Examples 86 and 87

The compounds listed in Table 21 were obtained in the same manner as in Example 85.

TABLE 21

| Example | R⁵ | Yield (%) | mp (°C.) | Recrystallizing Solvent |
|---------|----|-----------|----------|-------------------------|
| 86 | pyridyl-NHCOCH₂CH₂ | 20 | 210–202 | Dichloromethane-ethanol |
| 87 | morpholino-NCOCH₂CH₂ | 46 | 170–171 | Dichloromethane-ethanol |

Reference Examples 79 through 95

The compounds listed in Tables 22 and 23 were obtained in the same manner as in Reference Example 1.

TABLE 22

$$\begin{array}{c} R^5 \\ \diagdown \\ R^6 \end{array} \!\!=\!\! \begin{array}{c} N \\ \diagup \\ S \end{array} \!\!-\!\! NHCSNHSO_2R$$

| Reference Example | $R^5$ | $R^6$ | R | Yield (%) | mp (°C.) | Recrystallizing Solvent |
|---|---|---|---|---|---|---|
| 79 | tetrahydronaphthyl | —CH$_2$CO—Val—OMe | C$_6$H$_4$—Me | 100 | Note 1) Oily substance | |
| 80 | tetrahydronaphthyl | —CH$_2$CO—Ile—OBz | C$_6$H$_4$—Me | 88 | Note 2) Oily substance | |
| 81 | tetrahydronaphthyl | —CH$_2$CO—Gly—OEt | C$_6$H$_4$—Me | 94 | 184–185 | Ethyl acetate-diethylether |
| 82 | tetrahydronaphthyl | CH$_2$CH$_2$CO$_2$Et | C$_6$H$_4$—Me | 83 | 164–165 | Dichloromethane-ethanol |
| 83 | tetrahydronaphthyl | CH$_2$CH$_2$CONHEt | C$_6$H$_4$—Me | 88 | 128–129 | Methanol |
| 84 | tetrahydronaphthyl | CH$_2$CH$_2$CON(piperidinyl)CONH$_2$ | C$_6$H$_4$—Me | 63 | 183–184 | Dichloromethane-methanol |
| 85 | tetrahydronaphthyl | CH$_2$CH$_2$CONHCH(CH$_2$CH$_2$CO$_2$Et)CO$_2$Et | C$_6$H$_4$—Me | 76 | 102–103 | Ethyl acetate-hexane |
| 86 | 4-cyclohexylphenyl | CH$_2$CH$_2$CO$_2$Et | C$_6$H$_4$—Me | 87 | 113–114 | Dichloromethane-ethanol |
| 87 | 4-cyclohexylphenyl | (CH$_2$)$_3$CO$_2$Et | C$_6$H$_4$—Me | 71 | 163–164 | Dichloromethane-ethanol |
| 88 | 4-cyclohexylphenyl | Et | C$_6$H$_4$—Me | 81 | 181–182 | Dichloromethane-ethanol |
| 89 | 4-cyclohexylphenyl | $^n$C$_3$H$_7$ | C$_6$H$_4$—Me | 84 | 195–196 | Dichloromethane-ethanol |

TABLE 23

| Reference Example | R⁵ | R⁶ | R | Yield (%) | mp (°C.) | Recrystallizing Solvent |
|---|---|---|---|---|---|---|
| 90 | 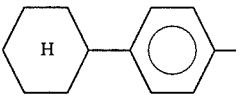 | Et | 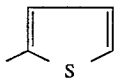 | 84 | 135–136 | Dichloromethane-ethanol |
| 91 | 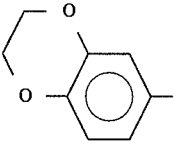 | Et | 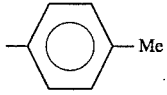 | 77 | 125–126 | Dichloromethane-ethanol |
| 92 | 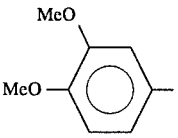 | Et | 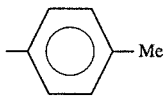 | 85 | 214–215 | Dimethylformamide-water |
| 93 | 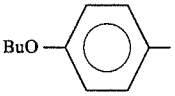 | Et | 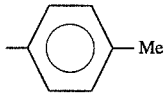 | 55 | 152–153 | Dichloromethane-ethanol |
| 94 | 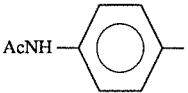 | Et | 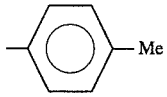 | 81 | 146–147 | Methanol-ethyl acetate |
| 95 | 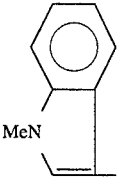 | Et | 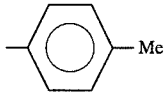 | 72 | 157–158 | Dichloromethane-methanol |

1) NMR (δ in DMSO-d₆): 0.87(3H, d, J=7 Hz), 1.7–1.9 (4H, m), 1.95–2.15(1H, m), 2.35(3H,s), 2.7–2.9 (4H,m), 3.63 (5H,s), 4.19 (1H, dd, J=8 and 6.5 Hz),7.1–7.4 (5H,m), 7.9–8.1 (2H,m), 8.48 (2H,d,J=8 Hz), 11.27 (1H, br s), 13.37 (1H,br s). 2) NMR (δ in DMSO-d₆): 0.81 (3H, t, J=8 Hz), 0.83 (3H,d,J=7 Hz), 1.0–1.5 (2H, m), 1.7–1.9 (5H,m), 2.35(3H,s), 2.7–2.9 (4H,m), 3.62(2H,br s), 4.2–4.3 (1H, m), 5.08(1H,d,J=2.5 Hz), 5.15 (1H,d,J=12.5 Hz), 7.1–7.5 (10H, m), 7.95–8.15(2H,m), 8.52(2,d,J=8 Hz), 11.31(1H,br s), 13.36 (1H,br s)

Reference Example 96

A mixture of N-[4-(4-cyclohexylphenyl)-5-methyl-2-thiazolyl]thiourea (1.00 g), 4-methoxy-2,6-dimethylphenylsulfonamide (1.30 g), potassium carbonate (500 mg) and xylene (40 ml) was refluxed with heating for 2 hours. After ethyl acetate (200 ml) was added, the mixture was washed with 2 N-hydrochloric acid and water and dried (magnesium sulfate), after which the solvent was distilled off. The residue was subjected to silica gel chromatography and eluted with methanol-chloroform (5:95, v/v) to yield a crystal of 1-[4-(4-cyclohexylphenyl)-5-methyl-2-thiazolyl]-3-(4-methoxy-2,6-dimethylphenylsulfonyl)- 2-thiourea (890 mg, yield 56%). This product was recrystallized from dichloromethane-methanol to yield a colorless prismatic crystal.

Melting point: 177° to 178° C.

Elemental analysis (for $C_{26}H_{31}N_3O_3S_3$): Calculated (%): C, 58.89; H, 5.90; N, 7.93 Found (%) : C, 58.55; H, 5.89; N, 7.93.

Reference Examples 97 through 105

The compounds listed in Table 24 were obtained in the same manner as in Reference Example 96.

TABLE 24

| Reference Example | R⁵ | R⁶ | R | Yield (%) | mp (°C.) | Recrystallizing Solvent |
|---|---|---|---|---|---|---|
| 97 | 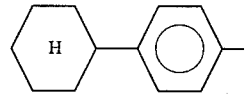 | Me | 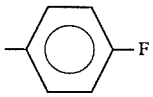 | 81 | 212–213 | Dichloromethane-methanol |

TABLE 24-continued

| Reference Example | R⁵ | R⁶ | R | Yield (%) | mp (°C.) | Recrystallizing Solvent |
|---|---|---|---|---|---|---|
| 98 | H-cyclohexyl-phenyl- | Me | pyridyl | 65 | Note 1) 266–267 | Chloroform-methanol |
| 99 | H-cyclohexyl-phenyl- | Me | pentamethylphenyl (Me×5) | 34 | 172–174 | Dichloromethane-methanol |
| 100 | H-cyclohexyl-phenyl- | Me | $^nC_3H_7$ | 49 | 180–181 | Dichloromethane-methanol |
| 101 | H-cyclohexyl-phenyl- | Me | $(CH_2)_7Me$ | 69 | 158–159 | Dichloromethane-methanol |
| 102 | H-cyclohexyl-phenyl- | Me | $Me_2CCH_2OH$ with $CH_2$ | 57 | 174–175 | Dichloromethane-methanol |
| 103 | H-cyclohexyl-phenyl- | Et | phenyl-F | 83 | 178–179 | Dichloromethane-methanol |
| 104 | H-cyclohexyl-phenyl- | Et | $Me_2CCH_2OH$ with $CH_2$ | 52 | 178–179 | Dichloromethane-methanol |
| 105 | H-cyclohexyl-phenyl- | Et | phenyl-$CO_2Me$ | 33 | 190–192 | Chloroform-methanol |

1)Potassium salt

Examples 88 through 117

The compounds listed in Tables 25 through 27 were obtained in the same manner as in Example 20.

TABLE 25

$$\begin{array}{c} R^5 \\ R^6 \end{array} \diagdown \begin{array}{c} N - S \\ S \end{array} \diagup \begin{array}{c} \\ N \end{array} \diagdown NSO_2R$$

| Example | R⁵ | R⁶ | R | Yield (%) | mp (°C.) | Recrystallizing Solvent |
|---|---|---|---|---|---|---|
| 88 | tetrahydronaphthyl | $-CH_2CO-Val-OMe$ | phenyl-Me | 77 | 190–191 | Dichloromethane-isopropyl ether |
| 89 | tetrahydronaphthyl | $-CH_2CO-Ile-OBz$ | phenyl-Me | 79 | Note 1) Oily substance | |

TABLE 25-continued $$\begin{array}{c} R^5 \\ \diagdown \\ R^6 \diagup \end{array} \begin{array}{c} N \text{---} S \\ \diagup \diagdown \\ S \diagdown \diagup N \end{array} NSO_2R$$

| Example | R⁵ | R⁶ | R | Yield (%) | mp (°C.) | Recrystallizing Solvent |
|---|---|---|---|---|---|---|
| 90 | tetrahydronaphthyl | —CH₂CO–Gly—OEt | 4-Me-C₆H₄ | 72 | 179–180 | Dichloromethane-ethyl acetate |
| 91 | tetrahydronaphthyl | CH₂CH₂CO₂Et | 4-Me-C₆H₄ | 53 | 107–108 | Dichloromethane-ethanol |
| 92 | tetrahydronaphthyl | CH₂CO₂H | 4-Me-C₆H₄ | Note 2) 33 | Note 3) 193–194 | Dichloromethane-methanol |
| 93 | tetrahydronaphthyl | CH₂CH₂CO₂H | 4-Me-C₆H₄ | Note 2) 27 | 160–161 | Chloroform-methanol |
| 94 | tetrahydronaphthyl | CH₂CH₂CONHEt | 4-Me-C₆H₄ | 48 | 187–188 | Dichloromethane-methanol |
| 95 | tetrahydronaphthyl | CH₂CH₂CON(piperidin-4-yl)CONH₂ | 4-Me-C₆H₄ | 74 | 222–223 | Dichloromethane-methanol |
| 96 | tetrahydronaphthyl | CH₂CH₂CONHCH(CH₂CH₂CO₂Et)CO₂Et | 4-Me-C₆H₄ | 86 | Note 4) Oily substance | |
| 97 | cyclohexyl-phenyl (H) | CH₂CH₂CO₂Et | 4-Me-C₆H₄ | 87 | 162–163 | Dichloromethane-methanol |

TABLE 26

| Example | R⁵ | R⁶ | R | Yield (%) | mp (°C.) | Recrystallizing Solvent |
|---|---|---|---|---|---|---|
| 98 | cyclohexyl-phenyl (H) | (CH₂)₃CO₂Et | 4-Me-C₆H₄ | 80 | 118–119 | Ethanol-hexane |
| 99 | cyclohexyl-phenyl (H) | Et | 4-Me-C₆H₄ | 78 | 158–159 | Dichloromethane-methanol |
| 100 | cyclohexyl-phenyl (H) | ⁿC₃H₇ | 4-Me-C₆H₄ | 79 | 164–165 | Dichloromethane-methanol |

TABLE 26-continued

| Example | R⁵ | R⁶ | R | Yield (%) | mp (°C.) | Recrystallizing Solvent |
|---|---|---|---|---|---|---|
| 101 | H-cyclohexyl-phenyl- | Et | 2-thienyl | 86 | 163–164 | Dichloromethane-methanol |
| 102 | 3,4-(OCH₂CH₂O)-phenyl- | Et | 4-Me-phenyl | 86 | 128–130 | Dichloromethane-methanol |
| 103 | 3,4-(MeO)₂-phenyl- | Et | 4-Me-phenyl | 85 | 187–188 | Dichloromethane-isopropyl ether |
| 104 | 4-BuO-phenyl- | Et | 4-Me-phenyl | 91 | 147–148 | Dichloromethane-methanol |
| 105 | 4-AcNH-phenyl- | Et | 4-Me-phenyl | 68 | 140–142 | Diethyl ether-isopropyl ether |
| 106 | N-Me-indol-yl | Et | 4-Me-phenyl | 68 | 123–125 | Dichloromethane-ethanol |
| 107 | H-cyclohexyl-phenyl- | Me | 3,5-Me₂-4-OMe-phenyl | 63 | 177–178 | Dichloromethane-methanol |
| 108 | H-cyclohexyl-phenyl- | Me | pyridyl | 60 | 165–166 | Dichloromethane-methanol |
| 109 | H-cyclohexyl-phenyl- | Me | 4-F-phenyl | 84 | 171–172 | Dichloromethane-ethanol |

TABLE 27

| Example | R⁵ | R⁶ | R | Yield (%) | mp (°C.) | Recrystallizing Solvent |
|---|---|---|---|---|---|---|
| 110 | H-phenyl-phenyl- | Me | 2,3,4,5,6-pentamethylphenyl- | 79 | 182–183 | Dichloromethane-methanol |
| 111 | H-phenyl-phenyl- | Me | ⁿC₃H₇ | 87 | 152–153 | Dichloromethane-isopropyl ether |
| 112 | H-phenyl-phenyl- | Me | (CH₂)₇Me | 91 | 141–142 | Dichloromethane-methanol |
| 113 | H-phenyl-phenyl- | Me | CH₂C(Me)₂CH₂OH | 84 | 170–171 | Dichloromethane-isopropyl ether |
| 114 | H-phenyl-phenyl- | Et | -phenyl-F | 86 | 200–201 | Dichloromethane-methanol |
| 115 | H-phenyl-phenyl- | Et | CH₂C(Me)₂CH₂OH | 78 | Note 5) Oily substance | |
| 116 | H-phenyl-phenyl- | Et | -phenyl-CO₂Me | 91 | Note 6) Oily substance | |
| 117 | H-phenyl-phenyl- | Et | (CH₂)₃CO₂Et | Note 2) 20 | 160–161 | Dichloromethane-isopropyl ether |

1) NMR (δ in CDCl₃): 0.86 (3H,d,J=7 Hz), 0.86 (3H,t,J=7 Hz), 1.0–1.4 (2H,m), 1.8–2.0 (5H,m), 2.38 (3H,s), 2.75–2.95 (4H,m), 3.67(2H,s), 4.64 (1H, dd,J=8.5 and 4.5 Hz), 5.12(1H,d,J=12 Hz), 5.22(1H,d,J=12 Hz), 6.21 (1H,d,J=8.5 Hz), 7.15–7.45 (10H,m), 7.77 (2H,d,J=8 Hz) 2) Yield from corresponding aminothiazole 3) Decomposed 4) NMR (δ in CDCl₃): 1.23 (3H,t,J=7 Hz), (3H,t,J=7 Hz), 1.75–2.45 (8H, m), 2.37 (3H,s), 2.54 (2H,t,J=7 Hz), 2.75–2.95 (4H,m), 3.08 (2H,t,J=7 Hz), 4.10 (2H,q,J=7 Hz), 4.18 (2H,t,J=7 Hz), 4.56 (1H,td,J=7.5 and 5 Hz), 6.48 (1H,d,J=7.5 Hz), 7.1–7.3 (5H,m), 7.76 (2H,d,J=8.5 Hz) 5) NMR (δ in CDCl₃): 1.11 (6H, s), 1.2–2.0 (13H,m), 2.5–2.7 (1H,m), 2.81 (2H,q,J=7.5 Hz), 3.18 (2H,s), 3.56 (2H,brs), 7.37 (4H,s). 6) NMR (δ in CDCl₃): 1.29 (3H,t,J=7.5 Hz), 1.2–2.0 (10H,m), 2.5–2.7 (1H,m), 2.81 (2H,q,J=7.5 Hz), 3.94 (3H,s), 7.40(4H,s), 7.97 (2H,d,J=8.5 Hz), 8.11 (2H,d,J=8.5 Hz)

Example 118

A crystal of N-[2-(3-indolyl)ethyl]-2-(4-methylphenyl)sulfonylimino-6-(5,6,7,8-tetrahydro-2-naphthyl)-2-naphthyl)-2H-thiazolo[3,2-b][1,2,4]thiadiazol-5-ylacetamide (195 mg, yield 20%) was obtained in the same manner as in Example 85. This product was recrystallized from chloroform-methanol to yield a colorless prismatic crystal.

Melting point: 210° to 211° C.

Elemental analysis (for C₃₃H₃₁N₅O₃S₃·0.5H₂O): Calculated (%): C, 60.90; H, 4.96; N, 10.76 Found(%): C, 61.09; H, 4.91; N, 10.66.

Formulation Examples (A) An endothelin receptor antagonist comprising as an active ingredient the compound represented by the formula (I') of the present invention or a pharmaceutically acceptable salt thereof can be used in accordance with, for example, the following formulations.

| 1. | Capsules | |
|---|---|---|
| (1) | the compound of Example 23 | 10 mg |
| (2) | lactose | 90 mg |
| (3) | fine crystalline cellulose | 70 mg |
| (4) | magnesium stearate | 10 mg |
| | one capsule | 180 mg |

(1), (2), (3) and a half of (4) are mixed and granulated. To the granules is added the remainder of (4), and the whole is filled into gelatin capsules.

61

| 2. | Tablets | |
|---|---|---|
| (1) | the compound of Example 23 | 10 mg |
| (2) | lactose | 35 mg |
| (3) | corn starch | 150 mg |
| (4) | fine crystalline cellulose | 30 mg |
| (5) | magnesium stearate | 5 mg |
| | one tablet | 230 mg |

(1), (2), (3), two thirds of (4) and a half of (5) are mixed and granulated. To the granules are added the remainders of (4) and (5), followed by subjecting the granules to compression molding.

| 3. | Injections | |
|---|---|---|
| (1) | a sodium salt of the compound of Example 39 | 10 mg |
| (2) | inositol | 100 mg |
| (3) | benzyl alcohol | 20 mg |
| | one ampoule | 130 mg |

(1), (2) and (3) are dissolved in distilled water for injection to make the whole volume 2 ml, which is filled into an ampoule. The whole process is conducted under sterile conditions.

(B) A cathepsin B inhibitor comprising as an active ingredient the compound represented by the formula (I') of the present invention or a pharmaceutically acceptable salt thereof can be used in accordance with, for example, the following formulations.

| 1. | Capsules | |
|---|---|---|
| (1) | the compound of Example 25 | 10 mg |
| (2) | lactose | 90 mg |
| (3) | fine crystalline cellulose | 70 mg |
| (4) | magnesium stearate | 10 mg |
| | one capsule | 180 mg |

(1), (2), (3) and a half of (4) are mixed and granulated. To the granules is added the remainder of (4), and the whole is filled into gelatin capsules.

| 2. | Tablets | |
|---|---|---|
| (1) | the compound of Example 25 | 10 mg |
| (2) | lactose | 35 mg |
| (3) | corn starch | 150 mg |
| (4) | fine crystalline cellulose | 30 mg |
| (5) | magnesium stearate | 5 mg |
| | one tablet | 230 mg |

(1), (2), (3), two thirds of (4) and a half of (5) are mixed and granulated. To the granules are added the remainders of (4) and (5), followed by subjecting the granules to compression molding.

| 3. | Injections | |
|---|---|---|
| (1) | a sodium salt of the compound of Example 39 | 10 mg |
| (2) | inositol | 100 mg |
| (3) | benzyl alcohol | 20 mg |
| | one ampoule | 130 mg |

(1), (2) and (3) are dissolved in distilled water for injection to make the whole volume 2 ml, which is filled into an ampoule. The whole process is conducted under sterile conditions.

62

(C) A bone resorption suppressor comprising as an active ingredient the compound represented by the formula (I') of the present invention or a pharmaceutically acceptable salt thereof can be used in accordance with, for example, the following formulations.

| 1. | Capsules | |
|---|---|---|
| (1) | the compound of Example 25 | 10 mg |
| (2) | lactose | 90 mg |
| (3) | fine crystalline cellulose | 70 mg |
| (4) | magnesium stearate | 10 mg |
| | one capsule | 180 mg |

(1), (2), (3) and a half of (4) are mixed and granulated. To the granules is added the remainder of (4), and the whole is filled into gelatin capsules.

| 2. | Tablets | |
|---|---|---|
| (1) | the compound of Example 25 | 10 mg |
| (2) | lactose | 35 mg |
| (3) | corn starch | 150 mg |
| (4) | fine crystalline cellulose | 30 mg |
| (5) | magnesium stearate | 5 mg |
| | one tablet | 230 mg |

(1), (2), (3), two thirds of (4) and a half of (5) are mixed and granulated. To the granules are added the remainders of (4) and (5), followed by subjecting the granules to compression molding.

| 3. | Injections | |
|---|---|---|
| (1) | a sodium salt of the compound of Example 39 | 10 mg |
| (2) | inositol | 100 mg |
| (3) | benzyl alcohol | 20 mg |
| | one ampoule | 130 mg |

(1), (2) and (3) are dissolved in distilled water for injection to make the whole volume 2 ml, which is filled into an ampoule. The whole process is conducted under sterile conditions.

What is claimed is:

1. A compound represented by the following formula (I''):

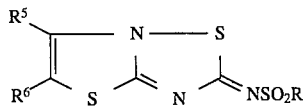

wherein R represents a hydrocarbon group or heterocyclic group which may be substituted; $R^5$ and $R^6$ independently represent hydrogen, halogen, a carboxyl group which may be esterified, or a hydrocarbon group which may be substituted; or a pharmaceutically acceptable salt thereof.

2. The compound according to claim 1, wherein the hydrocarbon group of R is an aliphatic chain hydrocarbon group or a monocyclic or condensed polycyclic aromatic hydrocarbon group.

3. The compound according to claim 2, wherein the aliphatic chain hydrocarbon group is a lower alkyl group.

4. The compound according to claim 2, wherein the monocyclic or condensed polycyclic aromatic hydrocarbon group is phenyl or naphthyl.

5. The compound according to claim 1, wherein the hydrocarbon group of $R^5$ and $R^6$ is an aliphatic chain hydrocarbon group or a monocyclic or condensed polycyclic aromatic hydrocarbon group.

6. The compound according to claim 5, wherein the aliphatic chain hydrocarbon group is a lower alkyl group.

7. The compound according to claim 5, wherein the monocyclic or condensed polycyclic aromatic hydrocarbon group is phenyl or naphthyl.

8. An endothelin receptor antagonist composition comprising as an active ingredient a compound represented by the following formula (I"):

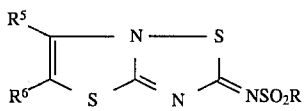

wherein R represents a hydrocarbon group which may be substituted; $R^5$ and $R^6$ independently represent hydrogen, halogen, a carboxyl group which may be esterified, or a hydrocarbon group which may be substituted; or a pharmaceutically acceptable salt thereof; and a pharmaceutically acceptable carrier.

9. The antagonist composition according to claim 8, wherein the hydrocarbon group of R is an aliphatic chain hydrocarbon group or a monocyclic or condensed polycyclic aromatic hydrocarbon group.

10. The antagonist composition according to claim 9, wherein the aliphatic chain hydrocarbon group is a lower alkyl group.

11. The antagonist composition according to claim 9, wherein the the monocyclic or condensed polycyclic aromatic hydrocarbon group is phenyl or naphthyl.

12. The antagonist composition according to claim 8, wherein the hydrocarbon group of $R^5$ and $R^6$ is an aliphatic chain hydrocarbon group or a monocyclic or condensed polycyclic aromatic hydrocarbon group.

13. The antagonist composition according to claim 12, wherein the aliphatic chain hydrocarbon group is a lower alkyl group.

14. The antagonist composition according to claim 12, wherein the monocyclic or condensed polycyclic aromatic hydrocarbon group is phenyl or naphthyl.

15. An cathepsin B inhibitor composition comprising as an active ingredient a compound represented by the following formula (I"):

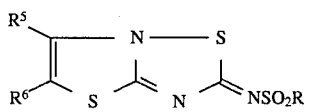

wherein R represents a hydrocarbon group which may be substituted; $R^5$ and $R^6$ independently represent hydrogen, halogen, a carboxyl group which may be esterified, or a hydrocarbon group which may be substituted; or a pharmaceutically acceptable salt thereof; and a pharmaceutically acceptable carrier.

16. A bone resorption suppressor composition containing as an active ingredient a compound represented by the following formula (I"):

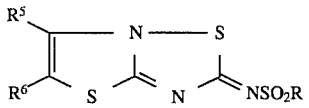

wherein R represents a hydrocarbon group which may be substituted; $R^5$ and $R^6$ independently represent hydrogen, halogen, a carboxyl group which may be esterified, or a hydrocarbon group which may be substituted; or a pharmaceutically acceptable salt thereof; and a pharmaceutically acceptable carrier.

* * * * *